(12) United States Patent
Spalding et al.

(10) Patent No.: US 6,858,774 B2
(45) Date of Patent: Feb. 22, 2005

(54) MDR-LIKE ABC TRANSPORTER GENE FROM PLANTS

(75) Inventors: Edgar P. Spalding, Madison, WI (US); Bosl Noh, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 162 days.

(21) Appl. No.: 09/817,762

(22) Filed: Mar. 26, 2001

(65) Prior Publication Data

US 2002/0068344 A1 Jun. 6, 2002

Related U.S. Application Data

(63) Continuation-in-part of application No. PCT/US99/22363, filed on Sep. 24, 1999.
(60) Provisional application No. 60/101,814, filed on Sep. 25, 1998.

(51) Int. Cl.[7] .................. C12N 15/09; C12N 15/29; C12N 15/82; A01H 5/00; A01H 5/10

(52) U.S. Cl. .................. 800/278; 800/298; 800/295; 800/306; 536/23.6; 536/24.1; 435/320.1; 435/419; 435/468

(58) Field of Search .................. 800/278, 298, 800/295, 306; 435/320.1, 419, 468; 536/24.1, 23.6

(56) References Cited

U.S. PATENT DOCUMENTS

| | | | |
|---|---|---|---|
| 5,073,677 A | 12/1991 | Helmer et al. | |
| 5,538,878 A | 7/1996 | Thomas et al. | |
| 5,786,162 A | 7/1998 | Corbisier et al. | |

OTHER PUBLICATIONS

Broun et al. "Catalytic Plasticity of Fatty Acid Modification Enzymes Underlying Chemical Diversity of Plant Lipids" Nov. 1998 Science vol. 282, pp 1315–1317.*

Lazar et al "Transforming Growth Factor x Mutation of Aspartic Acid 47 and Leucine 48 Results in Different Biological Activities" Mar. 1988 Molecular and Cellular Biology vol. 8 No. 3, pp 1247–1252.*

Sidler et al., *Involvement of an ABC Transporter in a Development Pathway Regulating Hypocotyl Cell Elongation in the Light*, The Plant Cell, Oct. 1998, vol. 10, pp. 1623–1636.

Davies et al., *Cloning and Characterization of a Novel P–Glycoprotein Homologue from Barley*, Gene, 1997, vol. 199, pp. 195–202.

Tommasini et al., *Differential Expression of Genes Coding for ABC Transporters After Treatment of Arabidopis Thaliana with Xenobiotics*, FEBS Letter, 1997, vol. 411, pp. 206–210.

Cho and Spalding, *An Amon Channel in Arabidopsis Hypocotyls Activated by Blue Light*, Proc. natl. Acad. Sci. USA, 93, 1996, pp. 8134–8138.

Dudler and Hertig, *Structure of an mdr–like gene from Arabidopsis Thaliana*, The Journal of Biological Chemistry, Mar. 25, 1992, vol. 267, No. 9, pp. 5882–5887.

* cited by examiner

Primary Examiner—Elizabeth F. McElwain
Assistant Examiner—Medina A. Ibrahim
(74) Attorney, Agent, or Firm—Woodcock Washburn LLP

(57) ABSTRACT

A novel plant gene is disclosed, which is a member of the mdr family of genes encoding ABC transporters. The gene is inducible by NPPB and auxin, and is preferentially expressed in roots upon induction. The gene is useful for detoxification of certain xenobiotics to protect plants from the detrimental effects of such compounds. The protein encoded by the gene is an auxin transporter. Also disclosed are plants the over-express and under-express this mdr gene.

17 Claims, 7 Drawing Sheets

```
hmdr1       1  MDLEGDRNGGAKKNF....FKLNNKSEKDKKEKKPT..VSVFSMFRYSNWLDKLYMVVGTLAAIIHGAGLPLMMLVFGEMTDIFANAGNLEDLMSNITNRSDINDTGFF
atpac       1  ~~~~~~~~~~~~~~~~MSETNTTDAKTVPAEAEKKREQSLPFFKLFSFADKFDYLLMFVGSLGAIVHGSSMPVFFLLFGQMVNGFGKNQMDL...............
consensus   1  md e   g  a            l  s  dr kkk     vgv lFryadw Dkl M lgtlaAilHGs lPlmmlvFgemtd fa           s
```

```
hmdr1     105  MN..LEEDMTRYAYYYSGIGAGVLVAAYIQVSFWCLAAGRQIHKIRKQFFHAIMRQEIGWFDVH.DVGELNTRLTDDVSKINEVIGDKIGMFFQSMATFFTGFIVGFTRG
mmdr1     102  SNSSLEEEMAIYAYYYTGIGAGVLIVAYIQVSLWCLAAGRQIHKIRQKFFHAIMNQEIGWFDVH.DVGELNTRLTDDVSKINDGIGDKIGMFFQSITTFLAGFIIGFISG
atpac      77  ..HQMVHEVSRYSLYFVYLGLVVCFSSYAEIACWMYSGERQVAALRKKYLEAVLKQDVGFFDTDARTGDIVFSVSTDFILVQDAISEKVGNFIHXLSTFLAGLVVGFVSA
atpgp1     80  ..EKMMEEVLKYALYFLVVGAAIWASSWAEISCWMWSGERQTTKMRIKYLEAALNQDIQFFDTEVRTSGDVMVQDAISEKLGNFIHYMATFVSGFIVGFTAV
atpgp2     73  ..KQASHRVAKYSLDFVYLSVAILFSSWLEVACWMHTGERQAAKMRRAYLRSSMLSQDISLFDTEASTGEVISAITSDILVVODALSEKVGNFLHYISRFIAGEAIGFTSV
consensus 111       k leeemtrIaYyysglgagvlv  ayiqvs W laaqRQirklR kffhailrQeigwFDi       tgelntrltdDiskindgigdKvGmFfq vatFlaGfivGFi g
```

```
hmdr3     214  WKLTLIVIMAISPILGLSAAVWAKILSAFSDKELAAYAKAGAVAEEALGAIRTVIAFGGQNKELERYQKHLENAKEIGIKKAISANISMGIAFLLIYASYALAFWYGSTLV
mmdr2     211  WKLTLIVIMAISPILGLSTAVWAKILSSTFSDKELAAYAKAGAVAEEAPGAIRTVIAFGGQNKELERYQKHLENAKKIGIKKAISANISMGIAFLLIYASYALAFWYGSTLV
hmdr1     212  WKLTLIVILAISPVIGLSAAVWAKILSFTDKELLAYAKAGAVAEEVLAAIRTVIAFGGQKELERYNKNLEEAKRIGIKKAITANISIGAAFLLIYASYALAFWYGTTLV
mmdr1     211  WKLTLVILAVSPLIGLSALWAKVLTSFTNKELQAYAKAGVABEVLAAIRTVIAFGGQKELERYNKNLEEAKNVGIKKAITASISIGIAYLLVYASYALAFWYGTSLV
atpac     185  WKLALLSVAVIPGIAFAGGLYAYTLTGITSKSRESYANAGVIAEQAIAQVRTVYSYVGESKALNAYSDAIQYTLKGLYKAGMAKGLGLGCTYGIACMSWALVFWYAGVFI
atpgp1    188  WQLALVTLAVVPLIAVIGGIHTTLSKLSNKSQESLSQAGNIVEQTVQIRVMAFVGESRASQAYSSALKIAQKLIQKTGLAKGMGLGATYFVVFCCYALLLWYGGYLV
atpgp2    181  WQISLVTLSIVPLIALAGGIYAFVAIGLIARVRKSYIKGEIABEVIGNVRTVQAFTGEERAVRLYREALENTYKYGRKAGLTKGLGLGSMHCVFLSWALLVWFTSVVV
consensus 221  WkltLvilaisPligLsaavwakils fs kel ayakAGavaEe  lgaiRtViafgGq  kelerYqk  le  akkiGikkaIsa  lsmG aflliyasYAlafWygstlv
```

W_A                                                                                                                SGC
```
hmdr3     324  ISKEYTIGNAMTVFFSILIGAFSVGQAAPCIDAFANARGAAYVIFDIITDNNPKIDSFSERGHKPDSIKGNLEFNDVHFSYPSRANVKILKGLMLKVQSGQTVALVGSSGC
mmdr2     321  ISKEYTIGNAMTVFFSILIGAFSVGQAAPCIDAFANARGAAYVIFDIIDNNPKIDSFSERGHKPDNIKGNLEFSDVHFSYPSRANIKILKGLMLKVKSGQTVALVGNSGC
hmdr1     322  LSGEYSIGQVLTVFFSVLIGAFSVGQASPSIEAPANARGAAYEIFKIIDNKPSIDSYSKSGHKPDNIKGNLEFRNVHFSYPSRKEVKILKGLMLKVQSGQTVALVGNSGC
mmdr1     321  LSNEYSIGEVLTVFFSILLGTFSIGHLAPNIEAFANARGAAFSKGKAAGYKLMEIINQRPTIQDPLDGKCLDQVHGNIEFKDVTFSYPSRPDVMIPRNENIFFPSGKTVAVVGGSGS
atpac     295  RNGQTDGGKAFTAIFSAIVGGMSLGQSFSNIGAGFSKGQSMAAFAKAVARAKIFRIIDHKPTIERNSESGVELDSVTGLVELKNVDFSYPSRPDVKILNNFCLSVPAGKTIALVGSSGS
atpgp1    298  RHHLTNGGLAIATMPAVMIGGLALGQSAPSMAAFAKAVARAAKIFRIIDHKPTIERNSESGVELDSVTGLVELKNVDFSYPSRPDVVIFDRLNLAIPAGKIVALVGGSGS
atpgp2    291  HKDIADGGKSFTTMLNVVIAGLSLGQAAPDISAFVRAKARAAYPIFKMIERNTVYKTSAKSGRKJGKVDGHIQFKDATFSYPSRPDVVIFDRLNLAIPAGKIVALVGGSGS
consensus 331  is  eytiG  amtvffsilligafsvGqaap idAFanargAay   idAFanargAay ifkiidn psidsfs  Ghkpd ikGnlefkdvhFsYPSr  evkilkglnlkv sGqtvAlvG SGc
```

FIGURE 1

```
hmdr3      434  GKSTTVQLIQRLYDPDEGTINIDGQDIRNFNVNYLREIIGVVSQEPVLFSTTIAENICYGRGNVTMDEIKKAVKEANAYEFIMKLPQKFDTLVGERGAQLSGGQKQRIAI
mmdr2      431  GKSTTVQLLQRLYDPTEGKISIDGQDIRNFNVRCLREIIGVVSQEPVLFSTTIAENIRYGRGNVTMDEIEKAVKEANAYDFIMKLPQKFDTLVGDRGAQLSGGQKQRIAI
hmdr1      432  GKSTTVQLMQRLYDPTEGMVSVDGQDIRTINVRFLREIIGVVSQEPVLFATTIAENIRYGRENVTMDEIEKAVKEANAYDFIMKLPHKFDTLVGERGAQLSGGQKQRIAI
mmdr1      431  GKSTTVQLMQRLYDPLEGVVSIDGQDIRTINVRYLREIIGVVSQEPVLFATTIAENIRYGREDVTMDEIEKAVKEANAYDFIMKLPHQFDTLVGERGAQLSGGQKQRIAI
atpac      405  GKSTVVSLIERFYDPNSGQILLDGVEIKTLQLKFLREQIGLVNQEPALFATTILENILYGKPDATMVEVEAAASANAHSFITLLPKGYDTVQVGERGVQLSGGQKQRIAI
atpgp1     408  GKSTVVSLIERFYDPNSGQVLLDGQDLKTLKLRWLRQQIGIVNQEPALFATSIKENILLGRPDADQVEIEEAARVANAHSFIIKLPDGFDTQVGERGLQLSGGQKQRIAI
atpgp2     401  GKSTVISLIERFYEPISGAVLLDGNNISELDIKWLRGQIGLVNQEPALFATTIRENILYGKDDATAEEITRAAKLSEAISFINNLPEGFETQVGERGIQLSGGQKQRIAI
consensus  441  GKSTtvqLiqRlYdP eG v iDGqdIrtinvrylReiIGvvsQEPvLfaTtiaENi yGr dvtmdEieKAvkeanAyeFimkLP fdtlVGeRGaQLSGGQKQRIAI W_B
hmdr3      544  ARALVRNPKILLLDEATSALDTESEAEVQAALDKAREGRTTIVIAHRLSTVRNADVIAGFEDGVIVEQGSHSELMKK..EGVYFKLVNMQTSGSQIQSEE........F.
mmdr2      541  ARALVRNPKILLLDEATSALDTESEAEVQAALDKAREGRTTIVIAHRLSTIRNADVIAGFEDGVIVEQGSHSELMKK..EGIYFRLVNMQTAGSQILSEE........FE
hmdr1      542  ARALVRNPKILLLDEATSALDTESEAVVQVALDKARKGRTTIVIAHRLSTVRNADVIAGFDDGVIVEKGNHDELMKE..KGIYFKLVTMQTAGNEVELEN........AA
mmdr1      541  ARALVRNPKILLLDEATSALDTESEAVVQAALDKAREGRTTIVIAHRLSTVRNADVIAGFDGGVIVEQGNHDELMRE..KGIYFKLVMTQTRGNEIEPGN........NA
atpac      515  ARAMLKDPKILLLDEATSALDASSESIVQEALDRVMVGRTTVVVAHRLCTIRNVDSIAVIQOGVVETGTHEELIAK..SGAYASLIRFQEMVGTRDFSNPSTRRTRSTR
atpgp1     518  ARAMLKNPAILLLDEATSALDSESEKLVQEALDRFMIGRTTLIIAHRLSTIRKADLVAVLQQGSVSEIGTHDELFSKGENGVYAKLIKMQEAAHETAMSNARKSSARPSS
atpgp2     511  SRAIVKNPSILLLDEATSALDAESEKSVQEALDRVMVGRTTVVVAHRLSTVRNADIIAVHEGKIVEFGNHENLIS.NPDGAYSSLLRIQETASLQRNPSLNRTLSRPHS
consensus  551  aRAlvrnPkILLLDEATSALDteSEavVQ ALDkar GRTTiViAhRLSTvRnaDviAgfedGvivE GsHdElmkk  GvYfklv mQt g i    n hmdr3      643  .ELNDEKAATRMAPNGWKSRLFRHSTQKNLKNSQMCQK...SLDVETDGLEANVPPVSFLKVLKLNKTEWPYFVVGTVCAIANGGLQPAFSVIFSEIIAIFGPGDD.AVK
mmdr2      641  VELSDEKAAGDVAPNGWKARIFRNSTKKSLKSPH..QN...RLDEETNELDANVPPVSFLKVLKLNKTEWPYFYVFVGTVCAIANGALQPAFSIILSEMIAIFGPGDD.AVK
hmdr1      642  DESKSEIDALEMSSNDSRSSLIRKRSTRRSVRGSQAQD...RKLSTKEALDESIPPVSFWRIMKLNLITEWPYFVVGFCAIINGLQPAFAIIFSKIIGVFTRIDDPETK
mmdr1      641  YGSQSDTDASELTSEESKSPLIR.RSIYRSVHRKQDQB...RRLSMKEAVDEDVPLVSFWRILMLNLSEWPYLLVGVLCAVINGCIQPVFAIVFSRIVGVFSRDDDHETK
atpac      623  LSHSLSTKSLSL....RSGSLRNLSYSYSTGADRIEBMISNAETORKTIRA...PENYFYRILLKLNSPEWPYSIMGAVGSILSGFIGPTFAIVMSNMIEVFYTYDYSME
atpgp1     628  ARNSVSSPIMTRNSSYGRSPYSRRLSDFSTSDFSLSIDASSYPNYRNEKLAFKDQANSFWRLAKQMNSPEWKYALLGSVGSVICGSLSAFFAYVLSAVLSVYYNPDHEYMI
atpgp2     620  IKYS........REJSRTRSSFCSER.ESVTRPDGADPSKKVKVTVG...RLYSMIRPDMYGVCGTICAFIAGSQMPLFALGVSQAL.VSYYSGWDETQ
consensus  661       s e a  m   ks l R s  s       qd  r d   d le  vp vsfwrvlkn teWpy vvgtvcaiing lqp Faills ilavf  dd  vk hmdr3      748  QQKCNIFSLIFLFLGIISFFTFFLQGFTFGKAGEILTRLRSMAFFKAMLRQDMSWFDDHKNSTGALSTRLATDAAQVQGATGTRLALIAQNIANLGTGIIISFIYGWQLT
mmdr2      745  QQKCNMFSLVFLGLGVLSFFTEFLQGFTFGKAGEILTRLRSMAFFKAMLRQDMSWFDDHKNSTGALSTRLATDAAQVQGATGTRLALIAQNTANLGTGIIISFIYGWQLT
hmdr1      749  RQNSNLFSLLFLALGIISFFTITFFLQGFTFGKAGEILTKRLRYMVFRSMLRQDMSWFDDPKNTTGALTTRLANDAASVKGAIGSRLAVTTONVANLGTGVILSIVYGWQLT
mmdr1      747  RQMCNLFSLFFIVMGLISFVTYFFQGFTFGKAGEILTKKRVRYMVFKSMLRQDISWFDDHKNSTGSLTTRLASDASSVKGAMGARLAVVTONVANLGTGVILSIVYGWQLT
atpac      725  RK.TKEYFIYIGAGLYAVGAYLIFNTLQHSFWDIVGENLTKRVREKMLSAVLNEMAWFDEDEHNSSLIAARLATDRADVKSAIAERISVIIQNMTSLLTSFIVAFIVEWRVS
atpgp1     738  KQ.IDKYCYLLIGLSSAAIVFNTLQHSFWDIVGENLTKRVREKMLSAVLQNEMAWFDQEENESARIAARLALDANNVRSAIGDRISVIVQNTALMLVACTAGFVIQWRLA
atpgp2     707  KE.IKKIAILFCCASVITLLIVYTIBHICFGTMGERLTLRVRENMFRAILLNEIGWFDEVDNTTSSMLASRLESDATLLKTIVVDRSTILLQNLGLVVTSFIAFILNWRLT
consensus  771  rq nifsliflgliisfltfflgftfgkaGEiLTrVr  mvfkamLrgdmsWFDd knstg lstRLatdAaqvkgalg rlavl QNlanlgtgiilsfiygWqlt
```

FIGURE 2

```
hmdr3      858  LLLLAVVPIIAVSGIVEMKLLAGNAKRDKKELEAAGKIATEAIENIRTVVSLTQERKFESMYVEKLYGPYRNSV..QKAHIYGITFSISQAFMYFSYAGCFRFGAYLIVN
mmdr2      855  LLLLSVVPFIAVAGIVEMKMLAGNAKRDKKEMEAAGKIATEAIENIRTVVSLTQERKFESMYVEKLHGPYRNSV..RKAHIYGITFSISQAFMYFSYAGCFRFGSYLIVN
hmdr1      859  LLLLAIVPIIAIAGVVEMKMLSGQALKDKKELEGAGKIATEAIENFRTVSLTQEQKFEHMYAQSLQVPYRNSL..RKAHIFGITFSFTQAMMYFSYAGCFRFGAYLVAH
mmdr1      857  LLVVIIPLIVLGGIIEMKLLSGQALKDKKQLEISGKIATEAIENFRTIVSLFCHELRVPQKRSLSLYRSQTSGFLFGLSQLALYGSEALIIWYGAHLVSK
atpac      834  LLILGTFPLLVLANFAQQLSLKGFAGDTAKAHAKTSMIAGEGVSNIRTVAAFNAQSKILSLFCHELRVPQKRSLSLYRSQTSGFLFGLSQLALYGSEALIIWYGAHLVSK
atpgp1     847  LVLVAFFPVVVAATVLQIFMTGFSGDLEAAHAKTQLAGERAIANVRTVAAFNSEAKIVRLYTAMLEPPLKR..CFWKGQIAGSGYGVAQFCLYASYALGLWYASWLVKH
atpgp2     816  LVVLATYPLIVISGHISEKLFMQGYGGDLNKAYLKANMLAGESVSNIRTVAAFCAEEKILELYSRELLEPSKSS..FRRGQIAGLFYGVSQFFIFSSYGLAWYGSTLMDK
consensus  881  Lllavv Piivvagivemkll Gna rdkk le agkiAtEaienNiRtvvslt e Kfesmy L Pyrnsv rkahlyGltfsisQa myfSyagcfrfgaylv h W_A
hmdr3      966  GHMRFRDVILVFSAIVFGAVALGHASSFAPDYAKAKLSAAHLFMLFERQPLIDSYSEEGL.KPDKFEGNITFNEVVENYPTRANVPVLQGLSLEVKKGQTLALVGSSGCG
mmdr2      963  GHMRFKDVILVFSAIVLGAVALGHASSFAPDYAKAKLSAAYLFSLFEROPLIDSYSGEGL.WPDKFEGSVTFNEVVENYPTRANVPVLQGLSLEVKKGQTLALVGSSGCG
hmdr1      967  KLMSFEDVLLVFSAVVFGAMAVGQVSSFAPDYAKAKISAAHIIMIIEKTPLIDSYSTEGL.MPNTLEGNVTFGEVVFNYPTRPDIPVLQGLSLEVKKGQTLALVGSSGCG
mmdr1      965  QLMTFENVMLVFSAVVFGAMAAGNTSSFAPDYAKAKVSASHIIRIIEKTPEIDSYSTEGL.KPTLLEGNVKFNGVQFNYPTRPNIPVLQGLSLEVKKGQTLALVGSSGCG
atpac      944  GVSTFSKVIKVFVVLVITANSVAETVSLAPEIIRGGEAVGSVFSVLDROTRIDPDDADAPV.ETIRGDIEFRHVDFAYPSRPDVMVFRDFNLRIRAGHSOALVGASGSG
atpgp1     955  GISDFSKTIRVFMVLMVSANGAAETLTLAPDFIKGGQAMRSVFELLDRKTEIEPDDPDTTPVPDRLRGEVELKHIDFSYPSRPDVVIFRDFDLIVRAGKTLALVGPSGCG
atpgp2     924  GLAGFKSVMKTFMVLIVTALAMGETLALAPDLLKGNOMVASVFEILDRKTQIV...GETSEELNNVEGTIELKGVHFSYPSRPDVIFRDFDLIVRAGKSMALVGQSGSG
consensus  991  glm F vilvFsaivgAvalg tssfAPdyakakl saa lf lier p ldsys egl pd leG v f v FnYPtRpdvpvlqglsLevkkGqtlALvGssGcG hmdr3      1075 KSTVVQLLERFYDPLAGTVLLDGQEEAKLNVQWLRAQLGIVSQEPILFDCSIAENIAYGDNSRVVSQDEIVSAAKAANIHPFIETLPHKYETRVGDKGTQLSGGQKQRIA
mmdr2      1072 KSTVVQLLERFYDPMAGSVLLDGQEAKKLNVQWLRAQLGIVSQEPILFDCSIAENIAYGDNSRVVPHDEIVRAAKEANIHPFIETLPQKYNTRVGDKGTQLSGGQKQRIA
hmdr1      1076 KSTVVQLLERFYDPLAGKVLLDGKEIKRLNVQWLRAHLGIVSQEPILFDCSIAENIAYGDNSRVVSQEEIVRAAKEANIHAFIESLPNKYSTKVGDKGTQLSGGQKQRIA
mmdr1      1074 KSTVVQLLERFYDPMAGSVFLDGKEIKQLNVQWLRAHLGIVSQEPILFDCSIAENIAYGDNSRAVSHEEIVRAAKEANIHQFIDSLPDKYNTRVGDKGTQLSGGQKQRIA
atpac      1053 KSSVIAMIERFYDPLLAGKVMIDGKDIRRLNLKSLRLKIGLVQQEPALFAATIFDNIAYGKDG..ATESEVIDAARAANAHGFISGLPEGYKTPVGERGVQLSGGQKQRIA
atpgp1     1065 KSSVISLIQRFYEPSSGRVMIDGKDIRKYNLKGAIRKHIAIVPQEPCLFGTTIYENIAYGHEC..ATEAEIIQAATLASAHKFISALPEGYKTVGERGVQLSGGQKQRIA
atpgp2     1031 KSSVISLILRFYDPTAGKVMIEGKDIKKLDLKALRKHIGLVQQEPALFATTIYENILYGNEG..ASQSEVVESAMLANAHSFITSLPEGYSTKVGRGVQMSGGQKQRIA
consensus  1101 KstvvqlleRFYdplaGkVlldGkeiklnvqwlRahlgiVsQEPilFdcslaeNIaYgdnsr vs dEiv aAk AnIH FletlpdKy TrVgdkGtQlSGGQKQRIA
```

MDR-LIKE ABC TRANSPORTER GENE FROM PLANTS

This application is a continuation in part of International Application No. PCT/US99/22363, filed Sep. 24, 1999, which claims priority under 35 U.S.C. §120 to U.S. Provisional Application 60/101,814 filed Sep. 25, 1998, the entireties of both of which are incorporated by reference herein.

Pursuant to 35 U.S.C. §202(c), it is acknowledged that the U.S. Government has certain rights in the invention described herein, which was made in part with funds from the National Science Foundation, Grant No. IBN-9416016.

FIELD OF THE INVENTION

This invention relates to the field of stress resistance in plants. In particular, the invention provides a novel gene from plants, which encodes an MDR-like ABC transporter, involved in detoxification of certain xenobiotics to protect plants from their detrimental effects.

BACKGROUND OF THE INVENTION

Several publications are referenced in this application to describe the state of the art to which the invention pertains. Each of these publications is incorporated by reference herein.

Environmental stress is one of the most important limitations on plant productivity, growth and survival. An ever-increasing source of environmental stress to plants is the stress caused by environmental pollutants in the soil, water and atmosphere. Such pollutants include herbicides, pesticides and related agronomic products, as well as organic and inorganic waste material from industry and other sources. Other toxic agents that threaten the survival of plants include various toxins produced by ephiphytic or soilborne microorganisms, such as fungi and bacteria.

In order to survive in toxic environments, plants must have mechanisms to detoxify xenobiotics, heavy metals and other toxic compounds. This generally involves modification of the toxic compound and subsequent excretion into the vacuole or apoplastic space. Recently, certain ATP-binding cassette (ABC) transporters have been identified in plants, which appear to be involved in the detoxification process.

The ABC transporter family is very large, with representatives existing in many different classes of organisms. Two well studied groups of ABC transporters, encoded by mdr and mrp genes, respectively, are associated with the multidrug resistance phenomenon observed in mammalian tumor cells. The mdr genes encode a family of P-glycoproteins that mediate the energy-dependent efflux of certain lipophilic drugs from cells. The mrp genes encode a family of transporters that mediate the extrusion of a variety of organic compounds after their conjugation with glutathione. YCF1, the yeast homolog of mrp, encodes a protein capable of glutathione-mediated detoxification of heavy metals.

Homologs of mrp and mdr genes have been identified in plant species. In *Arabidopsis thaliana*, the glutathione-conjugate transporter encoded by the mrp homolog is located in the vacuolar membrane and is responsible for sequestration of xenobiotics in the central vacuole (Tommasini et al., FEBS Lett. 411: 206–210, 1997; Li et al., Plant Physiol. 107: 1257–1268, 1995). An mdr-like gene (atpgp1) has also been identified in *A. thaliana*, which encodes a putative P-glycoprotein homolog. The atpgp1 gene was found to share significant sequence homology and structural organization with human mdr genes, and was expressed with particular abundance in inflorescence axes (Dudler & Hertig, J. Biol. Chem. 267: 5882–5888, 1992). Other MDR homologs have been found in potato (Wang et al., Plant Mol. Biol. 31: 683, 1996) and barley (Davies et al., Gene 199: 195, 1997).

The aforementioned mrp and mdr plant homologs were identified as a result of an effort to understand the molecular basis for development in plants of cross-resistance to herbicides of unrelated classes. However, these transporters are likely to serve the more general role in plants of sequestering, secreting, or otherwise detoxifying various organic and inorganic xenobiotics. Accordingly, it will constitute an advance in the art of plant genetic engineering of stress tolerance to identify and characterize other members of this class of transporters in plants.

SUMMARY OF THE INVENTION

In accordance with the present invention, a new plant mdr homolog, referred to herein as plPAC, has been identified. Unlike the previously identified plant mdr homologs, this new gene is inducible by a class of compounds known to inhibit chloride ion channels. The new gene is also inducible by auxin and binds NPA.

According to one aspect of the invention, a nucleic acid isolated from a plant is provided, which encodes a p-glycoprotein that is inducible by exposure of the plant to NPPB or auxin. The isolated nucleic acid is preferentially expressed in plant roots upon exposure of the plant to NPPB. In a preferred embodiment, the plant from which the nucleic acid is isolated is selected from the group consisting of *Brassica napus* and *Arabidopsis thaliana* and is 3850–4150 nucleotides in length. In a more preferred embodiment, the nucleic acid has the restriction sites shown in FIG. 4 for at least three restriction enzymes. In particularly preferred embodiments, the nucleic acid molecule encodes a polypeptide having SEQ ID NO:2. In an exemplary embodiment, the nucleic acid is a cDNA comprising the coding region of SEQ ID NO:1 or SEQ ID NO:10.

According to another aspect of the invention is an expression cassette that comprises a plPAC gene operably linked to a promoter, and in a more preferred embodiment the plPAC gene is from Arabidopsis. In preferred embodiments, the expression cassette comprises the cauliflower mosaic virus 35S promoter, and part of all of SEQ ID NO:1 or SEQ ID NO:10. Further included in this aspect is a vector comprising the expression cassette and a method for producing transgenic plants with the expression cassette and vector.

Another aspect of the invention is drawn to transgenic cells and plants containing the nucleic acids of the invention. In one preferred embodiment, the nucleic acids are be in the aforementioned expression cassette. Further included in this aspect are reproductive units from the transgenic plant.

According to another aspect of the invention, an isolated nucleic acid molecule is provided, which has a sequence selected from the group consisting of: a) SEQ ID NO:1 and SEQ ID NO:10; b) a nucleic acid sequence that is at least about 60% homologous to the coding regions of SEQ ID NO:1 or SEQ ID NO:10; c) a sequence hybridizing with SEQ ID NO:1 or SEQ ID NO:10 at moderate stringency; d) a sequence encoding part or all of a polypeptide having SEQ ID NO:2; e) a sequence encoding an amino acid sequence that is at least about 70% identical to SEQ ID NO:2; f) a sequence encoding an amino acid sequence that is at least about 80% similar to SEQ ID NO:2; g) a sequence encoding an amino acid sequence that is at least about 40% similar to residues 1–76, 613–669 or 1144–1161 of SEQ ID NO:2; and h) a sequence hybridizing at moderate stringency to a sequence encoding residues 1–76, 613–669 or 1144–1161 of SEQ ID NO:2. A polypeptide produced by expression of the above listed sequences is also provided.

According to another aspect of the invention, an isolated plant p-glycoprotein, which is inducible upon exposure of the plant to NPPB, is provided. The polypeptide preferably confers upon a cell in which it is found resistance to Rhodamine 6G. The polypeptide is preferentially produced in roots upon the exposure to the NPPB. The polypeptide is preferably from Brassica napus or Arabidopsis thaliana. In most preferred embodiments, the polypeptide has a sequence that is a) an amino acid sequence that is at least 80% similar to SEQ ID NO:2; b) an amino acid sequence that is at least 70% identical to SEQ ID NO:2; c) an amino acid sequence that is at least 40% similar to residues 1–76, 613–669 or 1144–1161 of SEQ ID NO:2; and d) an amino acid sequence encoded by a nucleic acid sequence hybridizing at moderate stringency to a amino acid sequence encoding residues 1–76, 613–669 or 1144–1161 of SEQ ID NO:2.

According to other aspects of the invention, antibodies immunologically specific for the polypeptides of the invention are provided, that immunologically specific to any of the polypeptides, of polypeptide encoded by the nucleic acids of the invention. In a preferred embodiment, the antibody is immunospecific to residues 1–76, 613–669 or 1144–1161 of SEQ ID NO:2.

According to another aspect of the invention, a plant p-glycoprotein gene promoter, which is inducible by NPPB, is also provided. In a preferred embodiment, the promoter is part or all of residues 1–3429 of SEQ ID NO:10. According to another aspect of the invention, plants that have reduces levels of plPAC protein are provided. In a preferred embodiment, these plants have mutations in the plPAC gene, and in a particularly preferred embodiment, the plPAC gene is mutated due to the insertion of a T-DNA. Also provided with this aspect is a method for selecting plants with mutations in plPAC using SEQ ID NOS:11–14 as PCR primers.

These and other features and advantages of the present invention will be described in greater detail in the description and examples set forth below.

BRIEF DESCRIPTION OF THE DRAWINGS

FIGS. 1–4. Amino acid sequence lineup of ATPAC deduced amino acid sequence and the amino acid sequences of related mammalian and plant genes. The lineup shows The ATPAC deduced amino acid sequence (SEQ ID NO:2) compared with (1) hmdr1 (SEQ ID NO:3); (2) mmdr1 (SEQ ID NO: 4); (3) hmdr3 (SEQ ID NO:5); (4) mmdr2 (SEQ ID NO:6); (5) atpgp1 (SEQ ID NO:7); and (6) atpgp2 (SEQ ID NO:8). A consensus sequence (SEQ ID NO: 9) is also shown. FIG. 1. Amino acids corresponding to 1–440 of the consensus sequence. FIG. 2. Amino acids corresponding to 441–880 of the consensus sequence. FIG. 3. Amino acids corresponding to 881–1210 of the consensus sequence. FIG. 4. Amino acids corresponding to 1211–1325 of the consensus sequence.

DETAILED DESCRIPTION OF THE INVENTION

I. Definitions

Figure 4:
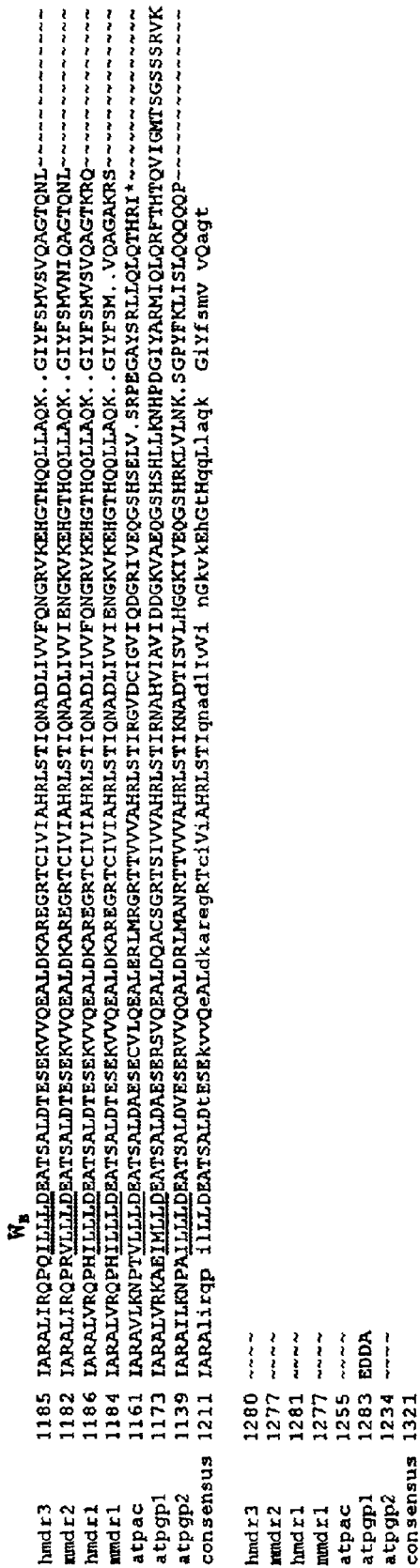

Various terms relating to the biological molecules of the present invention are used hereinabove and also throughout the specification and claims.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules of the invention the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below). Nucleic acid sequences and amino acid sequences can be compared using computer programs that align the similar sequences of the nucleic or amino acids thus define the differences. For purposes of this invention, the DNAStar program (DNAStar, Inc., Madison, Wis.) and the default parameters used by that program are the parameters intended to be used herein to compare sequence identity and similarity. Alternately, the Blastn and Blastp 2.0 programs provided by the National Center for Biotechnology Information (Altschul et al., 1990, J Mol Biol 215:403410) using a gapped alignment with default parameters, may be used to determine the level of identity and similarity between nucleic acid sequences and amino acid sequences.

The term "substantially the same" refers to nucleic acid or amino acid sequences having sequence variation that do not materially affect the nature of the protein (i.e. the structure, thermostability characteristics and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest, but which do not substantially recognize and bind other molecules in a sample containing a mixed population of antigenic biological molecules.

With respect to oligonucleotides, the term "specifically hybridizing" refers to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "expression cassette", as used herein, comprises 5' and 3' regulatory regions operably linked to a coding sequence. The coding sequence may be in the sense or antisense orientation with respect to the 5' regulatory region.

The term "promoter region" refers to the 5' regulatory regions of a gene.

The term "reporter gene" refers to genetic sequences which may be operably linked to a promoter region forming a transgene, such that expression of the reporter gene coding region is regulated by the promoter and expression of the transgene is readily assayed.

The term "selectable marker gene" refers to a gene product that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

The term "DNA construct" refers to genetic sequence used to transform plants and generate progeny transgenic plants. These constructs may be administered to plants in a viral or plasmid vector. Other methods of delivery such as Agrobacterium T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 2001.

The term "xenobiotic" refers to foreign chemicals or agents not produced or naturally found in the organism. The term is commonly used in reference to toxic or otherwise detrimental foreign chemicals, such as organic pollutants or heavy metals.

II. Description of plPAC and its Encoded Polyeptide

In accordance with the present invention, a nucleic acid encoding a novel ATP-binding-cassette (ABC) transporter has been isolated and cloned from plants. This novel ABC transporter is induced by auxin and binds NPA. The nucleic acid is referred to herein as plPAC.

A cDNA clone of the plPAC from *Arabidopsis thaliana*, an exemplary plPAC of the invention, is described in detail herein and its nucleotide sequence is set forth in Example 1 as SEQ ID NO:1. This nucleic acid molecule is referred to as "ATPAC". It is 36% identical and 51% similar to human mdr1 across the entire sequence. It is 51% identical to the atpgp1 gene reported by Dudler & Hertig (1997, supra) and 50% identical to atpgp2, a close homolog of atpgp1, published in the Genbank database. ATPAC protein is 65% similar to atpgp1 and atpgp2 proteins.

A partial clone of a plPAC of the invention was originally isolated from *Brassica napus* via differential expression screening of plants grown in the presence or absence of the chloride channel blocker, 5-nitro-2-(3-phenylpropylamino) benzoic acid (NPPB). A 0.5 kb gene fragment was identified, which had been up-regulated in response to NPPB treatment. This cDNA fragment was used to screen an Arabidopsis cDNA library, from which the complete ATPAC clone was isolated. The isolation and characterization of ATPAC is described in Example 1.

A genomic clone of ATPAC (SEQ ID NO:10) has also been isolated from a bacterial artificial chromosome (BAC) library of the Arabidopsis genome (BAC clone IGF F3J22, obtained from the Arabidopsis stock center, Ohio State University). A 7 kb fragment containing part of ATPAC and additional 5' regulatory sequences was subcloned into a plasmid vector (pBluescript). A restriction map of ATPAC is found in FIG. 6. The corresponding cDNA clone of ATPAC is found in SEQ ID NO:1 and its restriction map as FIG. 7.

In Arabidopsis, plPAC of the present invention is expressed in roots, leaves, flowers, and shoot meristem. Expression is strong in the hypocotyl of etiolated seedlings, but not in light grown seedlings. Expression of ATPAC is also relatively high in cotyledons, meristem, roots and the first true leaves of seedlings.

Among the unique features of this nucleic acid molecule as compared with other mdr-like genes from plants are its inducibility by certain compounds, including NPPB, herbicides and auxin, and its preferential expression in roots. The promoter regulatory region of ATPAC comprises residues 1–3429 of SEQ ID NO:10.

Although the ATPAC cDNA clone from *Arabidopsis thaliana* is described and exemplified herein, this invention is intended to encompass nucleic acid sequences and proteins from other plant species that are sufficiently similar to be used instead of ATPAC nucleic acid and proteins for the purposes described below. These include, but are not limited to, allelic variants and natural mutants of SEQ ID NO:1, which are likely to be found in different species of plants or varieties of Arabidopsis.

Because such variants are expected to possess certain differences in nucleotide and amino acid sequence, this invention provides an isolated plPAC nucleic acid molecule having at least about 60% (preferably 70% and more preferably over 80%) sequence homology in the coding regions with the nucleotide sequence set forth as SEQ ID NO:1 or SEQ ID NO:10 (and, most preferably, specifically comprising the coding region of SEQ ID NO:1). Also provided are nucleic acids that encode a polypeptide that is at least about 40% (preferably 50% and most preferably 60%) similar to residues 1–76, 613–669 or 1144–1161 of SEQ ID NO:2. Also provided are nucleic acids that hybridize to the nucleic acids of SEQ ID NO:1, SEQ ID NO:10, or nucleic acids encoding the regions of residues 1–76, 613–669 or 1144–1161 of SEQ ID NO:2, preferably under moderate stringency (more preferably, high stringency, and most preferably, very high stringency).

Figure 6:
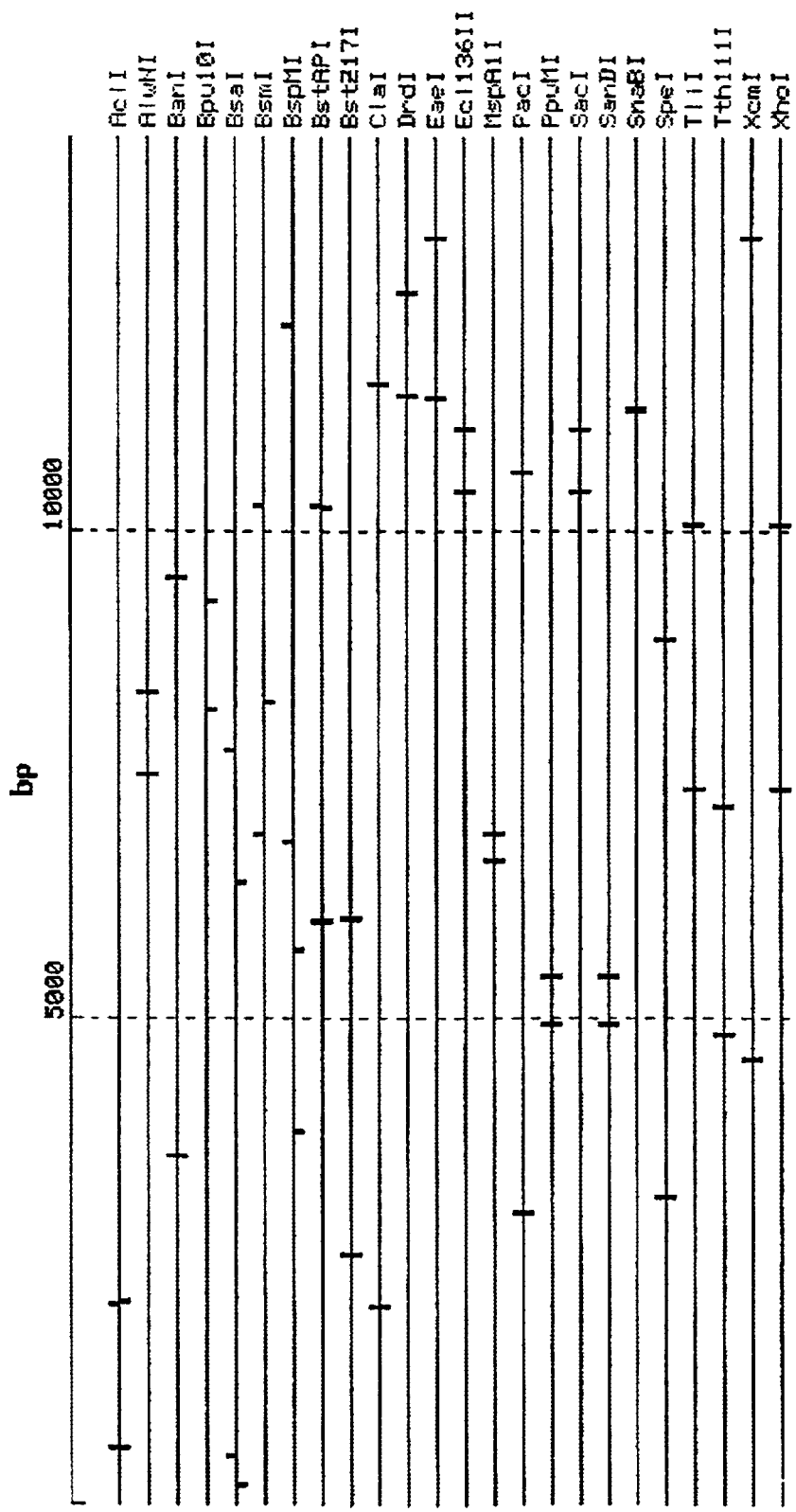
FIG. 6. Restriction map of genomic clone of ATPAC, SEQ ID NO:10.
Figure 7:
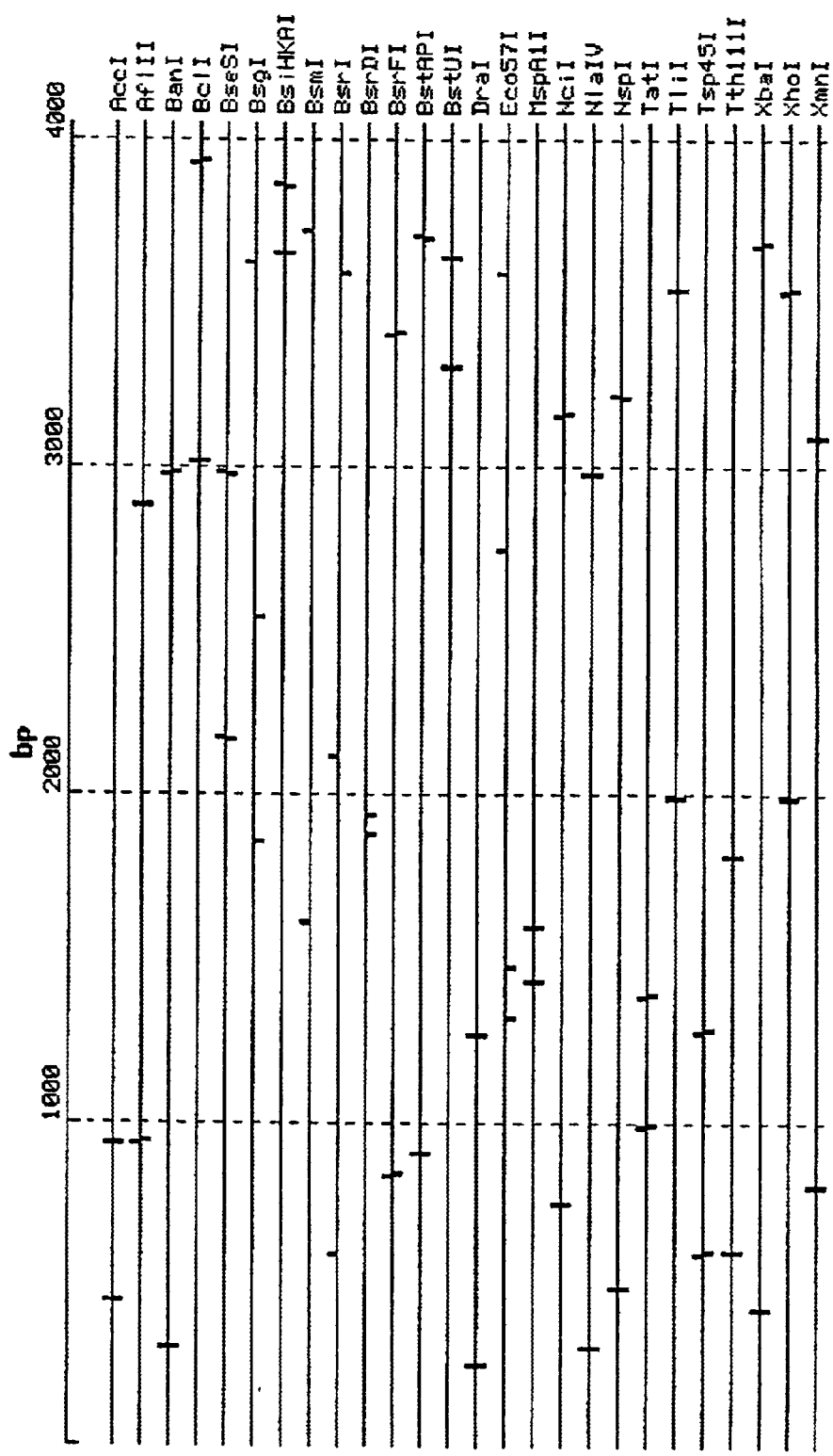
FIG. 7. Restriction map of cDNA clone of ATPAC, SEQ ID NO: 1.

In other preferred embodiments, the nucleic acids have a restriction digest map that is identical for at least 3 enzymes (more preferably 6 enzymes and most preferably 9 enzymes) to the maps shown in FIG. 6 or 7. In another preferred embodiment, the nucleic acids have a restriction digest map identical to those shown in FIG. 6 for enzymes XhoI, XcmI and SpeI (preferably additionally SacI, PacI and BsaI, and most preferably additionally AclI, BanI and SnaBI).

In another preferred embodiment, the nucleic acids have a restriction digest map identical to those shown in FIG. 7 for enzymes XbaI, TatI and NciI (preferably additionally DraI , BsmI and BclI, and most preferably additionally AccI , BsgI and TliI). The nucleic acids of the invention are at least 20 nucleic acids in length (preferably at least 50 nucleic acids and most preferably at least 100 nucleic acids).

In accordance with the invention, novel plPAC genes from two plant species, *Brassica napus* and *Arabidopsis thaliana*, are presented. This constitutes the first description of this unique p-glycoprotein in plants. Indeed, the closest known protein sequence, also from Arabidopsis, is only 65% identical suggesting that the ATPAC gene is novel and is expected to have novel properties. The isolation of two plPAC genes from different species enables the isolation of further plPAC genes from other plant species. Isolated nucleic acids that are plPAC genes from any plant species are considered part of the instant invention. In particular, the nucleic acids of other plPAC genes can be isolated using sequences of ATPAC that distinguish plPAC genes from other plant mdr genes according to methods that are well known to those in the art of gene isolation. In particular, sequences that encode residues 1–76, 613–669 and 1144–1161 of SEQ ID NO:2 can be used. In a preferred embodiment, the plPAC gene is from any higher plant species (more preferred from a dicot species, and most preferred from a species in Brassicaceae (or Cruciferae)).

This invention also provides isolated polypeptide products of the open reading frames of SEQ ID NO:1 or SEQ ID NO:10, having at least about 70% (preferably 80% and most preferably 90%) sequence identity, or at least about 80% similarity (preferably 90% and more preferably 95%) with the amino acid sequence of SEQ ID NO:2. In another embodiment, the polypeptides of the invention are at least about 40% identical (preferably 50%, and most preferably 60%) to the regions of residues 1–76, 613–669 or 1144–1161 of SEQ ID NO:2. Because of the natural sequence variation likely to exist among plPAC genes, one skilled in the art would expect to find up to about 30–40% nucleotide sequence variation, while still maintaining the unique properties of the plPAC gene and encoded polypeptide of the present invention. Such an expectation is due in part to the degeneracy of the genetic code, as well as to the known evolutionary success of conservative amino acid sequence variations, which do not appreciably alter the nature of the encoded protein. Accordingly, such variants are considered substantially the same as one another and are included within the scope of the present invention.

Also provided are transgenic plants transformed with part or all of the nucleic acids of the invention. Transgenic plants that over-express a plPAC coding sequence are one embodiment of this aspect of the invention. Example 3 provides for one prototype of such a plant. In a preferred embodiment, the ATPAC gene is used, and in a most preferred embodiment SEQ ID NO:1 or SEQ ID NO:10 is used. The plPAC gene may be placed under a powerful constitutive promoter, such as the Cauliflower Mosaic Virus (CaMV) 35S promoter or the figwort mosaic virus 35S promoter. In a preferred embodiment, the 35SCaMV promoter is used. Transgenic plants expressing the plPAC gene under an inducible promoter (either its own promoter or a heterologous promoter) are also contemplated to be within the scope of the present invention. Inducible plant promoters include the tetracycline repressor/operator controlled promoter. In a preferred embodiment, a native plPAC promoter is used, and in a most preferred embodiment, residues 1–3429 of SEQ ID NO:10 is used. Plant species that are contemplated for overexpression of a plPAC coding sequence include, but are not limited to, soybean.

In another embodiment, overexpression of plPAC is induced to generate a co-suppression effect. This excess expression serves to promote down-regulation of both endogenous and exogenous plPAC genes.

In some instances, it may be desirable to down-regulate or inhibit expression of endogenous plPAC in plants possessing the gene. Accordingly, plPAC nucleic acid molecules, or fragments thereof, may also be utilized to control the production of plPAC-encoded P-glycoproteins. In one embodiment, full-length plPAC antisense molecules or antisense oligonucleotides, targeted to specific regions of plPAC-encoded RNA that are critical for translation, are used. The use of antisense molecules to decrease expression levels of a pre-determined gene is known in the art. In a preferred embodiment, antisense molecules are provided in situ by transforming plant cells with a DNA construct which, upon transcription, produces the antisense sequences. Such constructs can be designed to produce full-length or partial antisense sequences. One example of antisense plPAC transgenic plants is given in Example 3.

In another embodiment, knock-out plants are obtained by screening a T-DNA mutagenized plant population for insertions in the plPAC gene (see Krysan et al., 1996, PNAS 93:8145). One example of this embodiment of the invention is found in Example 3. Optionally, transgenic plants can be created containing mutations in the region encoding the active site of plPAC. These last two embodiments are preferred over the use of anti-sense constructs due to the high homology among P-glycoproteins. The promoter of ATPAC is also provided in accordance with the invention. This promoter has the useful properties of root expression and inducability by NPPB. Presence of NPPB in the growth medium of Arabidopsis seedlings results in increased expression of ATPAC of the present invention.

Further, when approximately 4 kb of upstream ATPAC promoter DNA is fused to the GUS reporter gene and transformed into wild-type plants, GUS staining is strong in the hypocotyl of etiolated seedlings, but not in light grown seedlings. Further, expression is high in cotyledons, meristem, root, and the first true leaves of seedlings. Staining was also observed in flowers and the apical portion of the inflorescence.

The prototypic example of this aspect of the invention is residues 1–3429 of SEQ ID NO:10. It is anticipated that plPAC genes from other plant species will likewise exhibit the aforementioned useful properties. As these promoter regions can easily be isolated from the plPAC genes that are provided with the invention, all plant plPAC gene promoters are provided with the invention. The nucleic acids of the invention therefore include a nucleic acid molecule that is at least about 70% identical (preferably 80% and most preferably 90%) to the residues 1–3429 of SEQ ID NO:10. Also provided are nucleic acids that hybridize to the nucleic acid residues 1–3429 of SEQ ID NO:10 preferably under moderate stringency (more preferably, high stringency, and most preferably, very high stringency).

Thus, the PlPAC of the present invention encodes an ABC transporter that binds NPA and is involved with auxin transport in the plant. Mutants of Arabidopsis lacking ATPAC and double mutants lacking both ATPAC and AtPGP1 display morphological phenotypes consistent with their demonstrated impairments in polar auxin transport. It has been widely accepted that NPA-sensitive regulatory site and the auxin-conducting channel of the efflux carrier are separate molecular entities. Strong evidence indicates that PIN-like genes encode the auxin-conducting channel of the efflux carrier (Palme and Galweiler (1999) Curr. Op. Plant Biol. 2:375–381). However, as evidenced in Example 4 of the present invention, MDR-like genes are components of the NPA-sensitive regulatory site.

Expression of the plPAC gene of the present invention is inducible by auxin as described below in Example 4. Treatment of wild type Arabidopsis seedlings with 2,4-D or high concentrations of auxin result in plants with the same phenotype as that of ATPAC mutant plants. The strongly curved organs of the double mutant resemble the twisted forms induced by treatment of some dicots with herbicidal levels of the auxin analog, 2,4-D and in Arabidopsis by treatment with auxin transport inhibitors (Sieburth, (1999) Plant Physiol. 121: 1179–1190). This indicates that ATPAC of the present invention pumps auxin or auxin conjugates from sites of synthesis, such as the apical meristem and expanding cotyledons (Sachs, (1991) Development S1: 833–893). Under this model, tissues that express this pump would accumulate auxin as a result of the mutation and the altered auxin balance could be responsible for the altered growth patters typifying the ATPAC phenotype. Further support of this model is the similarity of auxin to indolylic substrates pumped by human MDR1, and the finding that ATPAC expression is increased by auxin. Also, the fact that NPA binds to ATPAC and that atpac knockout mutants can be phenocopied by auxin application suggests that ATPAC is an important component of the auxin transport and distribution machinery.

The present invention also provides antibodies capable of immunospecifically binding to polypeptides of the invention. In a preferred embodiment, the antibodies react immunospecifically with various epitopes of the plPAC-encoded polypeptides. In a particularly preferred embodiment, the antibodies are immunologically specific to the polypeptide of residues 1–76, 613–669 or 1144–1161 of SEQ ID NO:2.

The following sections sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (2001) (hereinafter "Ausubel et al.") are used.

III. Preparation of PlPAC Nucleic Acid Molecules, encoded Polypeptides, Antibodies Specific for the Polypeptides and Transgenic Plants 1. Nucleic Acid Molecules PlPAC nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as the cDNA having SEQ ID NO:1, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

PlPAC genes also may be isolated from appropriate biological sources using methods known in the art. In fact, the ATPAC clone was isolated from an Arabidopsis cDNA library using a partial clone obtained from *Brassica napus*. In alternative embodiments, genomic clones of plPAC may be isolated.

In accordance with the present invention, nucleic acids having the appropriate level sequence homology with part or all the coding regions of SEQ ID NO:1 or SEQ ID NO:10 may be identified by using hybridization and washing conditions of appropriate stringency. For example, hybridizations may be performed, according to the method of Sambrook et al., using a hybridization solution comprising: 5×SSC, 5×Denhardt's reagent, 1.0% SDS. 100 μg/ml denatured, fragmented salmon sperm DNA, 0.05% sodium pyrophosphate and up to 50% fomamide. Hybridization is carried out at 37–42 C for at least six hours. Following hybridization, filters are washed as follows: (1) 5 minutes at room temperature in 2×SSC and 1% SDS; (2) 15 minutes at room temperature in 2×SSC and 0.1% SDS; (3)30 minutes—1 hour at 37 C in 2×SSC and 0.1% SDS; (4) 2 hours at 45–55 C in 2×SSC and 0.1% SDS, changing the solution every 30 minutes.

One common formula for calculating the stringency conditions required to achieve hybridization between nucleic acid molecules of a specified sequence homology (Sambrook et al., 1989):

$T_m=81.5°$ C.$+16.6$ Log [Na+]$+0.41$(% G+C)$-0.63$ (% formamide)$-600/\#$bp in duplex As an illustration of the above formula, using [N+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20–25 C below the calculated Tm of the of the hybrid. Wash conditions should be as stringent as possible for the degree of identity of the probe for the target. In general, wash conditions are selected to be approximately 12–20 C below the Tm of the hybrid. In regards to the nucleic acids of the current invention, a moderate stringency hybridization is defined as hybridization in 6×SSC, 5×Derihardt's solution, 0.5% SDS and 100 µg/ml denatured salmon sperm DNA at 42 C, and wash in 2×SSC and 0.5% SDS at 55 C for 15 minutes. A high stringency hybridization is defined as hybridization in 6×SSC, 5×Denhardt's solution, 0.5% SDS and 100 µg/ml denatured salmon sperm DNA at 42 C, and wash in 1×SSC and 0.5% SDS at 65 C for 15 minutes. A very high stringency hybridization is defined as hybridization in 6×SSC, 5×Denhardt's solution, 0.5% SDS and 100 µg/ml denatured salmon sperm DNA at 42 C, and wash in 0.1×SSC and 0.5% SDS at 65 for 15 minutes.

Nucleic acids of the present invention may be maintained as DNA in any convenient cloning vector. In a preferred embodiment, clones are maintained in plasmid cloning/expression vector, such as pGEM-T (Promega Biotech, Madison, Wis.) or pBluescript (Stratagene, La Jolla, Calif.), either of which is propagated in a suitable E. coli host cell.

PlPAC nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of SEQ ID NO:1 or SEQ ID NO:10. Such oligonucleotides are useful as probes for detecting plPAC genes or mRNA in test samples, e.g. by PCR amplification, mapping of genes or for the positive or negative regulation of expression of plPAC genes at or before translation of the mRNA into proteins.

The plPAC promoter is also expected to be useful in connection with the present invention, inasmuch as it is inducible in plants upon exposure to anion channel blockers. As mentioned above, seven-kilobase fragment of genomic DNA has been isolated, which contains part or all of the plPAC promoter from *Arabidopsis thaliana*. This promoter can be used in chimeric gene constructs to facilitate inducible expression of any coding sequence of interest, upon exposure to NPPB or similar-acting compounds.

2. Proteins and Antibodies

Polypeptides encoded by plPAC nucleic acids of the invention may be prepared in a variety of ways, according to known methods. If produced in situ the polypeptides may be purified from appropriate sources, e.g., plant roots or other plant parts.

Alternatively, the availability of nucleic acid molecules encoding the polypeptides enables production of the proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md. According to a preferred embodiment, larger quantities of plPAC-encoded polypeptide may be produced by expression in a suitable procaryotic or eucaryotic system. For example, part or all of a DNA molecule, such as the cDNA having SEQ ID NO:1, may be inserted into a plasmid vector adapted for expression in a bacterial cell (such as E. coli) or a yeast cell (such as Saccharomyces cerevisiae), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The plPAC polypeptide produced by gene expression in a recombinant procaryotic or eucyarotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The plPAC-encoded polypeptides of the invention, prepared by the aforementioned methods, may be analyzed according to standard procedures.

Polyclonal or monoclonal antibodies directed toward any of the peptides encoded by plPAC may be prepared according to standard methods. Monoclonal antibodies may be prepared according to general methods of Köhler and Milstein, following standard protocols.

C. Transgenic Plants

Transgenic plants expressing the plPAC gene can be generated using standard plant transformation methods known to those skilled in the art. These include, but are not limited to, Agrobacterium vectors, PEG treatment of protoplasts, biolistic DNA delivery, UV laser microbeam, gemini virus vectors, calcium phosphate treatment of protoplasts, electroporation of isolated protoplasts, agitation of cell suspensions with microbeads coated with the transforming DNA, direct DNA uptake, liposome-mediated DNA uptake, and the like. Such methods have been published in the art. See, e.g., *Methods for Plant Molecular Biology* (Weissbach & Weissbach, eds., 1988); *Methods in Plant Molecular Biology* (Schuler & Zielinski, eds., 1989); *Plant Molecular Biology Manual* (Gelvin, Schilperoort, Verma, eds., 1993); and *Methods in Plant Molecular Biology—A Laboratory Manual* (Maliga, Klessig, Cashmore, Gruissem & Varner, eds., 1994).

The method of transformation depends upon the plant to be transformed. The biolistic DNA delivery method is useful for nuclear transformation. In another embodiment of the invention, Agrobacterium vectors are used to advantage for efficient transformation of plant nuclei.

In a preferred embodiment, the gene is introduced into plant nuclei in Agrobacterium binary vectors. Such vectors include, but are not limited to, BIN19 (Bevan, 1984, Nucleic Acid Res 12: 8711–8721) and derivatives thereof, the pBI vector series (Jefferson et al., 1987, PNAS 83:844751), and binary vectors pGA482 and pGA492 (An, 1986) and others (for review, see An, 1995, Methods Mol Biol 44:47–58). In preferred embodiments, the pPZP211 vector (Hajdukiewicz et al., 1994, PMB 25:989994) or PCGN7366 (Calgene, Calif.) are used. DNA constructs for transforming a selected plant comprise a coding sequence of interest operably linked to appropriate 5' (e.g., promoters and translational regulatory sequences) and 3' regulatory sequences (e.g., terminators).

DNA constructs for transforming a selected plant comprise a coding sequence of interest operably linked to appropriate 5' (e.g., promoters and translational regulatory sequences) and 3' regulatory sequences (e.g., terminators). In a preferred embodiment, the coding region is placed under a powerful constitutive promoter, such as the Cauliflower Mosaic Virus (CaMV) 35S promoter or the figwort mosaic virus 35S promoter. Other constitutive promoters contemplated for use in the present invention include, but are not limited to: T-DNA mannopine synthetase, nopaline synthase (NOS) and octopine synthase (OCS) promoters.

Transgenic plants expressing a sense or antisense SDS coding sequence under an inducible promoter are also contemplated to be within the scope of the present invention. Inducible plant promoters include the tetracycline repressor/operator controlled promoter, the heat shock gene promoters, stress (e.g., wounding)-induced promoters, defense responsive gene promoters (e.g. phenylalanine ammonia lyase genes), wound induced gene promoters (e.g. hydroxyproline rich cell wall protein genes), chemically-inducible gene promoters (e.g., nitrate reductase genes, glucanase genes, chitinase genes, etc.) and dark-inducible gene promoters (e.g., asparagine synthetase gene) to name a few.

Tissue specific and development-specific promoters are also contemplated for use in the present invention. Examples of these included, but are not limited to: the ribulose bisphosphate carboxylase (RuBisCo) small subunit gene promoters or chlorophyll a/b binding protein (CAB) gene promoters for expression in photosynthetic tissue; the various seed storage protein gene promoters for expression in seeds; and the root-specific glutamine synthetase gene promoters where expression in roots is desired.

The coding region is also operably linked to an appropriate 3' regulatory sequence. In a preferred embodiment, the nopaline synthetase polyadenylation region (NOS) is used. Other useful 3' regulatory regions include, but are not limited to the octopine (OCS) polyadenylation region.

Using an Agrobacterium binary vector system for transformation, the plPAC coding region, under control of a constitutive or inducible promoter as described above, is linked to a nuclear drug resistance marker, such as kanamycin resistance. Agrobacterium-mediated transformation of plant nuclei is accomplished according to the following procedure:

(1) the gene is inserted into the selected Agrobacterium binary vector;

(2) transformation is accomplished by co-cultivation of plant tissue (e.g., leaf discs) with a suspension of recombinant Agrobacterium, followed by incubation (e.g., two days) on growth medium in the absence of the drug used as the selective medium (see, e.g., Horsch et al. 1985, Cold Spring Harb Symp Quant Biol. 50:4337);

(3) plant tissue is then transferred onto the selective medium to identify transformed tissue; and (4) identified transformants are regenerated to intact plants.

It should be recognized that the amount of expression, as well as the tissue specificity of expression of the plPAC gene in transformed plants can vary depending on the position of their insertion into the nuclear genome. Such position effects are well known in the art. For this reason, several nuclear transformants should be regenerated and tested for expression of the transgene.

IV. Uses of PlPAC Nucleic Acids, Encoded Proteins and Antibodies

1. PlPAC Nucleic Acids

PlPAC nucleic acids may be used for a variety of purposes in accordance with the present invention. The DNA, RNA, or fragments thereof may be used as probes to detect the presence of and/or expression of plPAC genes. Methods in which plPAC nucleic acids may be utilized as probes for such assays include, but are not limited to: (1) in situ hybridization; (2) Southern hybridization (3) northern hybridization; and (4) assorted amplification reactions such as polymerase chain reactions (PCR).

The PlPAC nucleic acids of the invention may also be utilized as probes to identify related genes from other plant species. As is well known in the art and described above, hybridization stringencies may be adjusted to allow hybridization of nucleic acid probes with complementary sequences of varying degrees of homology. Thus, plPAC nucleic acids may be used to advantage to identify and characterize other genes of varying degrees of relation to the exemplary ATPAC, thereby enabling further characterization of this family of genes in plants. Additionally, they may be used to identify genes encoding proteins that interact with the P-glycoprotein encoded by plPAC (e.g., by the "interaction trap" technique).

Further, as described below, the genes or antisense molecules may be used to produce transgenic plants that have altered responses to herbicides and auxin.

2. PlPAC Proteins and Antibodies

Purified plPAC-encoded P-glycoproteins, or fragments thereof, may be used to produce polyclonal or monoclonal antibodies which also may serve as sensitive detection reagents for the presence and accumulation of plant P-glycoproteins in cultured plant cells or tissues and in intact plants. Recombinant techniques enable expression of fusion proteins containing part or all of the plPAC-encoded protein. The full length protein or fragments of the protein may be used to advantage to generate an array of monoclonal or polyclonal antibodies specific for various epitopes of the protein, thereby providing even greater sensitivity for detection of the protein in cells or tissue.

Polyclonal or monoclonal antibodies immunologically specific for plPAC-encoded proteins may be used in a variety of assays designed to detect and quantitate the protein. Such assays include, but are not limited to: (1) flow cytometric analysis; (2) immunochemical localization in cultured cells or tissues; and (3) immunoblot analysis (e.g., dot blot, Western blot) of extracts from various cells and tissues.

Polyclonal or monoclonal antibodies that immunospecifically interact with one or more of the polypeptides encoded by plPAC can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

3. plPAC Transgenic Plants

Transgenic plants that over- or under-express plPAC can be used in a varied of agronomic and research applications.

From the foregoing discussion, it can be seen that plPAC and its homologs, and transgenic plants containing them will be useful for improving stress resistance or tolerance in plants. This provides an avenue for developing marginal or toxic soil environments for crop production. Both over- and under-expressing plPAC transgenic plants have great utility in the research of herbicides and other xenobiotic compounds.

As discussed above and in greater detail in Example 1, the similarity between plant and mammalian mdr genes indicates that their functional aspects will also be conserved. Thus, plPAC is expected to play an important role in the exclusion of toxic metabolic or xenobiotic compounds from cells. The fact that plPAC also is inducible and appears to be preferentially expressed in roots, where contact with such compounds often occurs, makes plPAC particularly desirable for genetic engineering of plants to increase their tolerance to such compounds. Accordingly, plants engineered to overexpress the plPAC gene should be resistant to a wide range of chemicals, both intentionally applied as herbicides or unintentionally as wastes. Examples of the kinds of xenobiotics that should be detoxified by the plPAC of the invention include, but are not limited to, hydrophobic (i.e., lipophilic) herbicides and other compounds, such as 3(3,4-dichlorophenyl)-1,1, dimethyl urea (also known as DCMU or Diuron, available from Sigma Chemical Co., St. Louis, Mo.) or other hydrophobic compounds that disrupt photosynthetic electron transport, as well as Metachlor (Ciba Geigy, Basel Switzerland), Taurocholate (Sigma Chemical Co.), Primisulfuron (Ciba Geigy), and IRL-1803.

As illustrated in Example 2, plant cells that over-express a plPAC gene have surprisingly higher growth rate with or without the xenobiotic compound Rhodamine 6G. It is contemplated that plPAC overexpression may be a generally useful way to increase plant and plant cell culture growth, even without the presence of xenobiotic compounds.

In addition to the above-mentioned features and advantages of transgenic plants that are altered in their expression of plPAC, these plants will also be altered in auxin transport. Through the use of developmental or tissue specific promoters, plants having a pre-determined alteration in auxin transport may be produced, providing agronomically or horticulturally beneficial features to such plants.

The following specific examples are provided to illustrate embodiments of the invention. They are not intended to limit the scope of the invention in any way.

EXAMPLE 1

Cloning and Analysis of a PlPAC from *Arabidopsis thaliana*

The plPAC of the present invention was identified by its up-regulation in response to a chloride ion channel blocker. *Brassica napus* plants were grown either in the presence or absence of 20 µM 5-nitro-2-(3-phenylpropylamino) benzoic acid (NPPB). After five days, the roots of the seedlings were harvested and total RNA was extracted separately from the treated and untreated plants. From the total RNA preparations, poly (A)+ RNA was isolated and used as the starting material to create a cDNA subtraction library, using the CLONTECH PCR-SELECTJ cDNA Subtraction Kit and accompanying instructions (CLONTECH Laboratories, Inc., Palo Alto, Calif.).

Using the subtractive hybridization kit, a gene fragment was identified that was up-regulated in response to treatment of the plants with NPPB. This fragment (0.5 kb) was used to screen a cDNA library of *Arabidopsis thaliana*, from which a full-length cDNA clone was isolated. The nucleotide sequence of this cDNA clone, referred to as ATPAC (*Arabidopsis thaliana* putative anion channel) is set forth below as SEQ ID NO:1.

The 3.76 kb cDNA clone encodes a polypeptide 1,254 amino acids in length. The deduced amino acid sequence encoded by SEQ ID NO:1 is shown an FIGS. 1–4 as "atpac" (SEQ ID NO:2), in a lineup with the following sequences: (1) hmdr1 (SEQ ID NO:3); (2) mmdr1 (SEQ ID NO:4); (3) hmdr3 (SEQ ID NO:5), (4) mmdr2 (SEQ ID NO:6); (5) atpgp1 (SEQ ID NO:7); and (6) atpgp2 (SEQ ID NO:8). A consensus sequence (SEQ ID NO.9) is also shown.

A search of various sequence databases indicates that ATPAC is a new and distinct member of the mdr family of ABC transporters. In none of the databases, including the EST collection, does an exact match exist. The ABC transporter family is very large, consisting of at least two sub-groups, mrp and homologs and mdr and homologs. The only examples of plant mdr-like genes are atpgp1 and atpgp2 from *A. thaliana* and two homologs from potato and barley, respectively. Though the atpgp1 and atpgp2 genes are similar to ATPAC, they are only 51 and 50% identical, respectively, indicating that ATPAC is a distinct gene by comparison. Sequence homology with the potato and barley mdr-like genes is even more divergent. Another difference between the agpgp1 gene and the ATPAC gene is their respective preferential expression in inflorescens and roots, respectively.

EXAMPLE 2

Figure 5:
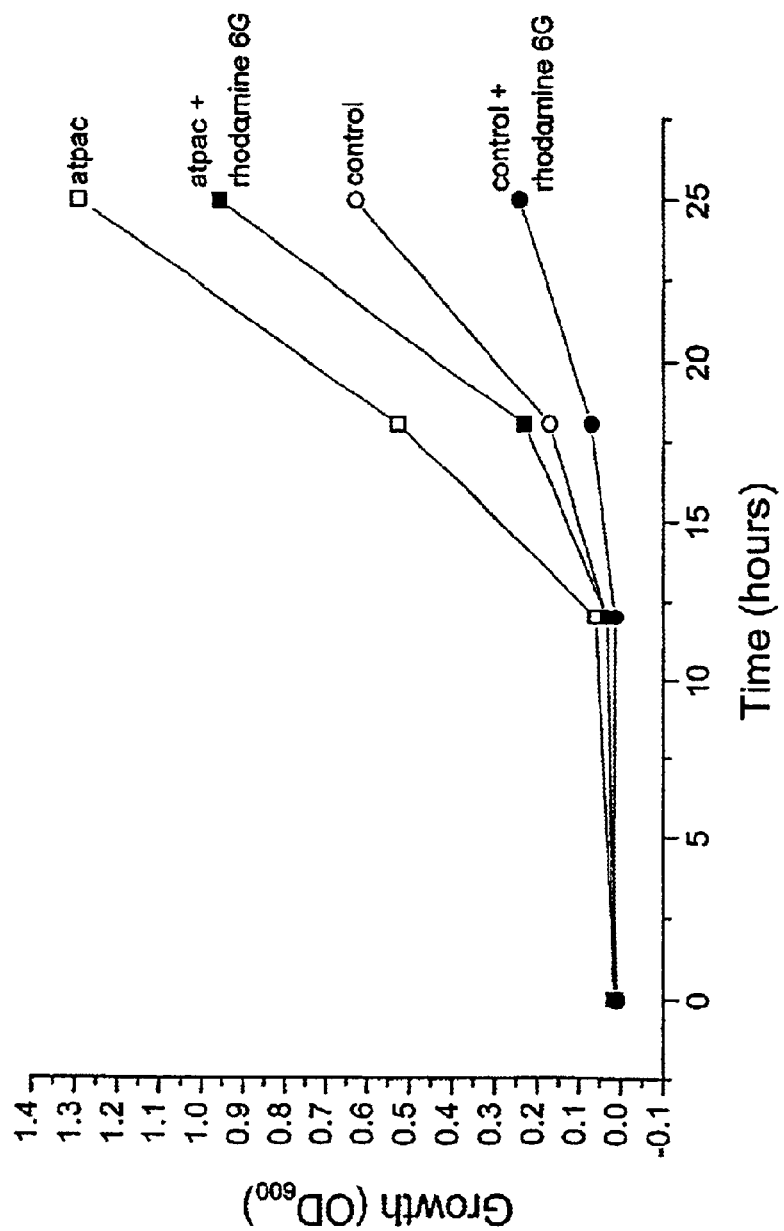
FIG. 5. Graph depicting the effect of rhodamine 6G on the growth rate of cells transformed with and expressing ATPAC as compared with control cells not containing ATPAC.

Effect of ATPAC Expression in Bacterial Cells on Their Ability to Detoxify Rhodamine 6G The compound Rhodamine 6G is a well known substrate of mammalian p-glycoproteins (Kolaczkowski et al., J. Biol. Chem. 271: 31543–31548, 1996). The ability of a cell to deroxify the compound is indicative of activity of p-glycoproteins. A bacterial cell line was transformed with an expression vector comprising ATPAC. The growth rate of transformed and non-transformed cells was then measured, in the presence or absence of Rhodamine 6G. Results are shown in FIG. 5. As can be seen, ATPAC-expressing cells grown in the absence of the drug had the best growth rate. Moreover, even in the presence of the drug, the cells grew more quickly than non-transformed cells in the presence or absence of Rhodamine 6G. These results demonstrate that ATPAC encodes a functional and robust p-glycoprotein.

EXAMPLE 3

Transgenic Plants that Overexpress and Underexpress ATPAC

Transformation construct. The Agrobacterium binary vector pPZP211 (Hajdukiewicz et al., 1994 Plant Mol. Biol. 25:989994) was digested with EcoRI and SmaI, and selfligated. This molecule was named pPZP211'. The Agrobacterium binary vector pCGN7366 (Calgene, Calif.) was digested with XhoI and cloned in SalIdigested pPZP211'. We named this binary vector pPZPPCGN. The 3.8 kb full-length ATPAC cDNA was cloned into the pGH19 vector. After digestion with SmaI (in the multiple cloning site upstream) and EcoRI, a 3.1 kb cDNA fragment was cut out. This SmaIEcoRI 3.1 kb fragment was cloned into the SmaI/EcoRI site of pPZPpCGN. The rest of ATPAC gene was amplified using polymerase chain reaction to have translationally fused HAtag at its 3'terminal. After ligating EcoR1 linkers to the ends of the resulting PCR product, the 0.7 kb fragment was cloned into the EcoRI site of the SmaIEcoRI 3.1 kb ATPAC fragment in pPZP-pCGN. The final construct was named pATPACOE.

Plant transformation. pATPACOE was introduced into Agrobacterium tumefaciens strain by a direct transformation method. Agrobacterium-mediated transformation was performed using vacuum infiltration (Bechtold et al., 1993,. CR Acad. Sci. [III] 316: 11941199.)

T1 plants which survived on kanamycincontaining plates were selected, transplanted into soil and grown to set T2 seed. T3 seeds were collected from kanamycinresistant T2 plants. T3 plants which showed 100% kanamycinresistance were selected and were considered homozygous for the transgene.

Antisense Plants. The full length cDNA in pBluescript SK( ) vector (Stratagene, Calif.) is digested with EcoRI (there is a cleavage site in the upstream polylinker) and SspI. The resulting 1.3 Kb fragment representing a 5' portion of the AtPAC cDNA was cloned into the aforementioned pPZPPCGN, which had been digested with EcoRI/SmaI, ensuring that this fragment of the cDNA was inserted in the antisense orientation. This construct was named pATPACAE. pATPACAE was introduced into Arabidopsis plants by Agrobacterium transformation, as described above.

Knock-out Plants. The method of Krysan et al (1996, PNAS 93:8145, incorporated by reference herein) was followed using the following primers:

Genespecific Primers:

AtpacF: CACTGCTCAATGATCTCGTTTTCTCACTA (SEQ ID NO:11)
AtpacR: CTTGAATCACACCAATGCAATCAACACCTC (SEQ ID NO:12)

Primers for TDNA left boarder:

JL202: CATTTTATAATAACGCTGCGGACATCTAC (SEQ ID NO:13)
JL270: TTTCTCCATATTGACCATCATACTCATTG (SEQ ID NO:14)

T-DNA insertion mutants were isolated by PCR-based screening of DNA pools. Two alleles of ATPAC and one ATPGP1 allele were isolated. At the seedling stage, both alleles of ATPAC displayed down-folded, or epinastic cotyledons and abnormally angled cotyledon petioles. The petioles of the cotyledons and first true leaves in ATPAC were shorter than in wild type plants. As adult plants, the rosette leaves were somewhat curled and wrinkled along the margin. Bolting of the inflorescence stem was delayed by 2.8 days on average, relative to wild-type. The bolt grew more slowly than wild type after starting, though the wild type length was utimately reached. These phenotypes coincided with the sites of expression indicated by GUS staining (as described herein). None of these phenotypes were present in plants transformed with a genomic fragment containing the wild type ATPAC promoter and coding sequence ("atpac1—1"). This mutant did not display any overt phenotype as a seedling or an adult plant. Double mutants were constructed by crossing atpac1—1 and atpgp1—1 plants. F1 individuals appeared wild type and were permitted to self pollinate. Approximately one in sixteen of the F2 seedlings displayed extremely down-curved cotyledons when grown in the light and also displayed shorter, wavy hypocotyls when grown in the dark. PCR analysis confirmed that these seedlings were homozygous double mutants. The adult double mutant plants were severely stunted in growth. Primary inflorescence stems of the double mutants and floral pedicels were also wavy in appearance, indicating that the direction of growth periodically changed during the elongation phase of these organs. After 72 hours of growth, the double mutant produced abundant secondary inflorescence stems, indicating a large reduction in apical dominance. Fertility of the flowers in the double mutants was poor, due to improper elongation of the stamen filament. Hand-pollinating flowers of the doubly homozygous mutant plants produced double-mutant seeds that were both viable and normal in appearance.

EXAMPLE 4

Effect of Auxin (IAA) on ATPAC Expression

Expression in Yeast and Xenopus Oocytes. ATPAC cDNA was expressed in wild type yeast as well as in yeasts lacking seven ABC transporters (as described by Decottignies et al., (1998) J. Biol. Chem. 273:12612–22)in order to create a heterologous system for studying function of the transporter. The yeasts were exposed to toxic compounds that are known substrates for human MDR1. ATPAC did not confer any measurable resistance to the toxic substrates. Further, there was no evidence of a drug-pumping role for ATPAC.

In order to examine whether ATPAC functions as an anion chanel or a regulator of an anion channel, complementary RNA made from an ATPAC cDNA template was injected into Xenopus oocytes to produce a heterologous expression system amenable to electrophysiology. No currents associated with ATPAC were observed by two electrode voltage clamping.

Treatment of wild type seedlings with 2,4-D or high concentrations of auxin result in plants having strongly curved organs.

ATPAC Binds the Auxin Transport Inhibitor naphthylphthalamic acid (NPA). Yeast expressing ATPAC was assayed for NPA binding. NPA bound tightly and specifically to ATPAC-expressing yeast, but not to control yeast. Bound NPA was not displaced by benzoic acid, a related hydrophobic organic acid. Proteins that bind NPA and influence auxin transport are considered important regulators of hormone action and therefore, of plant development. The fact that NPA binds to ATPAC and that atpac knockout mutants can be phenocopied by auxin application suggests that ATPAC is an important component of the auxin transport and distribution machinery.

Effect of ATPAC and AtPGP1 on Auxin Transport.

Three different auxin transport assays of the Ws wild type, ATPAC-1, ATPAC-2 and atpgp1 were performed. The first measured the basipetal movement of auxin in seedlings as described by Murphy et al. (2000) Planta 211:315–324. A 0.1 µl microdroplet of radioactive auxin was placed on the apex of a light-grown seedling. Four hours later, the amount of radioactivity collected on moist filter paper that contacted the root tip was determined. Polar auxin transport measured in this manner was severely reduced in both alleles of ATPAC and especially in the double mutant, but not in the atpgp1 mutant.

The second assay measured the basipetal transport of radioactive auxin through etiolated seedlings inverted in a reservoir containing radioactive auxin (Garbers et al. (1996) EMBO J. 15:2115–2124). The results were similar to those with the first assay described above.

The third assay measured basipetal transport of auxin in the inflorescence stem in a method described by Ruegger et al (1997) Plant Cell 9:745–57. A segment of inflorescence stem was excised and immersed apical-end down in a tube containing a small volume of radioactive auxin. At a later time, a piece of tissue was excised from the basal end of the segment and counted in a scintillation counter. Seedlings having ATPAC mutations clearly displayed defective auxin transport profiles. Further, the atpgp1 mutation significantly impaired transport in tissue segments taken from the lower portion of the inflorescence. This is indicative of gradients of function of at least two MDR-like gene products along the inflorescence axis.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated nucleic acid molecule having a sequence selected from the group consisting of:
   a) SEQ ID NO:1 or SEQ ID NO:10;
   b) a nucleic acid sequence encoding a p-glycoprotein with xenobiotic detoxification activity, wherein the nucleic acid is at least about 95% identical to the coding regions of SEQ ID NO:1 or SEQ ID NO:10;
   c) a nucleic acid sequence encoding a polypeptide having SEQ ID NO:2; and
   d) a nucleic acid sequence encoding a p-glycoprotein with xenobiotic detoxification activity with an amino acid sequence that is at least about 95% identical to SEQ ID NO:2.

2. The isolated nucleic acid of claim 1, which is expressed in a plant upon exposure of the plant to 5-nitro-2-(3-phenylpropylamino) benzoic acid (NPPB).

3. The isolated nucleic acid of claim 2, which is expressed in plant roots upon exposuire of the plant to NPPB.

4. The isolated nucleic acid of claim 1, wherein the plant is Brassica napia or Arabidopsis thaliana and wherein the nucleic acid is 3850–4150 nucleotides long.

5. An expression cassette, which comprises the isolated nucleotide molecule of claim 1 operably linked to a promoter.

6. The expression cassette of claim 5, which comprises plPAC gene from Arabidopsis thaliana.

7. The expression cassette of claim 6, wherein the promoter is the cauliflower mosaic virus 35S promoter.

8. The expression cassette of claim 6, wherein the plPAC gene is about 95% identical to the coding sequence of SEQ ID NO:1 or SEQ ID NO:10.

9. A vector comprising the expression cassette of claim 5.

10. The vector of claim 9, which is comprised of an Agrobacterium binary vector selected from the group consisting of pPZP211 and pCGN7366.

11. A transgenic plant comprising the expression cassette of claim 5 wherein the plant has enhanced resistance to xenobiotic compounds.

12. A seed from the transgenic plant of claim 11, said seed comprising the expression cassette.

13. A cell from the transgenic plant of claim 11, said cell comprising the expression cassette.

14. A recombinant DNA molecule comprising the nucleic acid molecule of claim 1, inserted in a vector for transforming cells.

15. A cell transformed with the recombinant DNA molecule of claim 14.

16. The cell of claim 15, selected from the group consisting of bacterial cells, yeast cells and plant cells.

17. A transgenic plant regenerated from the transformed plant cell of claim 16.

* * * * *

SEQUENCE LISTING

<160> NUMBER OF SEQ ID NOS: 14

<210> SEQ ID NO 1
<211> LENGTH: 4051
<212> TYPE: DNA
<213> ORGANISM: Arabidopsis thaliana
<220> FEATURE:
<221> NAME/KEY: misc_feature
<222> LOCATION: (94)...(0)
<223> OTHER INFORMATION: Translation start codon
<221> NAME/KEY: misc_feature
<222> LOCATION: (3932)...(0)
<223> OTHER INFORMATION: Stop codon

<400> SEQUENCE: 1

```
cttgaacttc acaaaacaat tgtcagattt tcaagaaaaa ctttataaaa caaaaaacat      60
ttcattcttt ctctctctct ctctcactgc tcaatgatct cgttttctca ctaaaccaac     120
tcgtttcttc ttactttctt taactcggat ctacaaaaaa ccatgtcgga aactaacaca     180
accgatgcca agactgttcc agcagaagca gagaagaaga aagaacagag tttaccattc     240
tttaaactct tttctttcgc tgataaattt gattatctct taatgttcgt tggttctctt     300
ggtgccattg ttcatggctc ttccatgcct gtcttctttt tactctttgg tcaaatggtt     360
aatggatttg gtaaaaacca aatggattta catcaaatgg ttcatgaagt ctctagatat     420
tctctatatt tcgtctactt gggtttggtc gtttgcttct cttcttacgc agagatagca     480
tgttggatgt attctggaga aagacaagta gcagcattaa ggaagaaata tcttgaagca     540
gtattaaaac aagacgttgg gttctttgat actgatgcta gaactggtga cattgtcttt     600
agtgtttcta ctgatactct tcttgttcaa gatgccatta gtgaaaaggt tggaaacttt     660
atacattacc tctcaacatt tttggcggga ttagtagttg gatttgtatc agcatggaaa     720
ttagctttgt taagtgttgc tgtgattccc ggaatcgctt tcgccggagg tttatacgct     780
tatacactca ccggaattac ttcaaagagc cgtgaatctt atgctaacgc cggtgttatc     840
gccgagcagg caattgctca agttcgaact gtttattctt atgttggaga gagtaaggca     900
cttaatgcgt attcggatgc gattcagtat acgcttaagc tcggttataa agcggggatg     960
gctaaagggt tgggtttagg atgtacttat ggaatagctt gtatgtcatg ggctttggtg    1020
ttttggtatg ctggagtttt tattcggaat ggacaaaccg atggaggaaa ggcgtttact    1080
gctatattct ctgctattgt tggtggaatg agtttggggc aatctttctc gaatcttggg    1140
gcgtttagta aaggtaaagc ggctggttat aagttgatgg agataattaa ccagagaccg    1200
acgataattc aagacccgtt ggatggaaaa tgtttggatc aagttcatgg gaacattgag    1260
tttaaagatg tgacttttag ctatccttca cggcctgatg ttatgatctt caggaacttt    1320 aatatttttct tcccttctgg gaaaactgtg gcggttgttg gtgggagtgg ctctggaaag    1380
```

-continued

```
agtactgttg tttccctcat tgagagattc tatgatccaa acagcgggca aattctgttg    1440
gatggtgttg agataaagac gcttcagttg aagttttttgc gtgaacaaat cgggcttgtg   1500
aatcaagaac ctgcgctctt tgccactact atactagaga acatactcta tggaaagcct   1560
gatgcaacaa tggttgaagt tgaagctgct gcttccgctg cgaatgcgca tagtttcatt   1620
acattacttc ctaaaggcta cgacacacag gttggagaac gtggtgttca actctcaggt   1680
ggacagaagc agagaattgc aattgctagg gcgatgttga agacccaaa gattctgtta   1740 ctagatgaag ctacaagcgc tcttgatgct agctctgaga gcattgttca ggaagcttta   1800
gacagagtca tggtggggag gaccactgtt gttgttgctc atcgtctctg caccatcaga   1860
aatgttgatt ccattgccgt gatacagcaa ggccaagttg ttgaaaccgg aacacatgaa   1920
gaactcattg ccaaatccgg tgcttacgca tccctcatca ggtttcagga atggttggt   1980 actcgagatt tctcaaaccc gtcaactcgt cgcactcgtt caacccgttt gagccattca   2040
ctgtcaacga atcactcag tttaagatca ggaagtttga ggaatctgag ctattcttac   2100
agcactggag ctgatggtcg gatagagatg atttcaaatg cagagactga ccgaaagact   2160
cgtgcccctg aaaattactt ctacaggctt ctcaagctta attccggga tggccttac   2220 tcaatcatgg gagcagtagg ctcaattctt tctggttca ttggtcctac atttgctatt   2280
gtgatgagca acatgatcga agtcttctac tacacagact atgattcaat ggaaaggaaa   2340
acaaaagagt atgtcttcat ctacattggt gctggtctct atgctgtggg tgcttatttg   2400
atccaacatt acttctttag catcatggga gaaaacctca caacaagagt aagaagaatg   2460
atgctctcag ctatcttgag aaacgaagtt ggttggttcg atgaggatga acacaactca   2520
agcctgatcg ctgcacgttt agctactgat gcagcagatg ttaaatccgc tatagccgag   2580
agaatctcag taattctaca aaacatgact tcacttctca catccttcat agtcgccttc   2640
atagtagaat ggagagtctc acttctcatc ttaggcacat tcccacttct agtcctcgct   2700
aactttgctc agcaactatc tctgaagggt tttgctggag acacagctaa ggctcatgca   2760
aagacttcaa tgattgctgg tgaaggagtc agtaacatta gaccgtagc agctttcaat   2820 gcacagagca agattctctc tttgttctgt catgagcttc gtgtacctca gaaaagaagc   2880
ttaagcttat accgaagtca aacctcgggt ttcctatttg gcctctcgca gcttgctctc   2940
tatggttctg aggctttaat tctctggtat ggtgcccacc ttgtgagtaa aggcgtgtca   3000
acctttccca aagtgatcaa agtgtttgtg gttttggtca ttactgcaaa ctctgttgct   3060
gaaactgtca gtcttgctcc tgaaattatt cggggaggtg aagctgttgg ttcggttttc   3120
tcggtcttgg acaggcagac caggattgac ccggatgatg ctgatgctga tcccgtggag   3180
acgatccgtg gagacattga gtttaggcat gttgatttcg cttaccctc aagacccgac   3240 gtcatggttt tcagggactt taacctcaga attcgagctg acatagcca agctcttgtg   3300 ggcgcgagtg ggtcagggaa gagttctgta attgcgatga tcgagcggtt ttacgacctt   3360
cttgctggaa aagtcatgat tgatggcaaa gacatccgcc ggctaaacct gaaatctcta   3420
aggctcaaaa tcggtcttgt tcaacaagaa ccagctcttt tcgcagcaac gatcttcgac   3480
aacatcgcct atggtaaaga tggtgcaact gaatccgagg taattgatgc agctcgagcc   3540
gcaaatgctc acgtttcat cagtggttta cctgaaggtt acaaaactcc agtaggcgaa   3600
agaggagtgc agttatcagg tggacagaaa cagaggatcg cgatagcaag agctgtgctc   3660 aagaaccta cagtgttgct tctagacgaa gcaactagcg cactagatgc agaatcagaa   3720
tgcgtgctgc aagaggcgtt agagaggctc atgagaggtc ggaccaccgt ggtagttgct   3780
```

-continued

```
caccgcttgt ccaccataag aggtgttgat tgcattggtg tgattcaaga cgggcggatt    3840
gtggagcaag gcagccattc agagctcgtt agccgaccag agggagctta ttcaaggctg    3900
ttacagcttc aaacacatag gatttgaagc ttgatcatgg attaaaaaca aaaatcggt     3960 ttgtgtaatt ttttttatat taaaacttta atttggaaga tttctatgga ctataacgat    4020
aatatgaata ggtgtagata atgaagcttt t                                   4051
```

<210> SEQ ID NO 2
<211> LENGTH: 1254
<212> TYPE: PRT
<213> ORGANISM: Arabidopsis thaliana

<400> SEQUENCE: 2

```
Met Ser Glu Thr Asn Thr Thr Asp Ala Lys Thr Val Pro Ala Glu Ala
 1               5                  10                  15

Glu Lys Lys Lys Glu Gln Ser Leu Pro Phe Phe Lys Leu Phe Ser Phe
            20                  25                  30

Ala Asp Lys Phe Asp Tyr Leu Leu Met Phe Val Gly Ser Leu Gly Ala
        35                  40                  45

Ile Val His Gly Ser Ser Met Pro Val Phe Phe Leu Leu Phe Gly Gln
    50                  55                  60

Met Val Asn Gly Phe Gly Lys Asn Gln Met Asp Leu His Gln Met Val
65                  70                  75                  80

His Glu Val Ser Arg Tyr Ser Leu Tyr Phe Val Tyr Leu Gly Leu Val
                85                  90                  95

Val Cys Phe Ser Ser Tyr Ala Glu Ile Ala Cys Trp Met Tyr Ser Gly
            100                 105                 110

Glu Arg Gln Val Ala Ala Leu Arg Lys Lys Tyr Leu Glu Ala Val Leu
        115                 120                 125

Lys Gln Asp Val Gly Phe Phe Asp Thr Asp Ala Arg Thr Gly Asp Ile
    130                 135                 140

Val Phe Ser Val Ser Thr Asp Thr Leu Leu Val Gln Asp Ala Ile Ser
145                 150                 155                 160

Glu Lys Val Gly Asn Phe Ile His Tyr Leu Ser Thr Phe Leu Ala Gly
                165                 170                 175

Leu Val Val Gly Phe Val Ser Ala Trp Lys Leu Ala Leu Leu Ser Val
            180                 185                 190

Ala Val Ile Pro Gly Ile Ala Phe Ala Gly Gly Leu Tyr Ala Tyr Thr
        195                 200                 205

Leu Thr Gly Ile Thr Ser Lys Ser Arg Glu Ser Tyr Ala Asn Ala Gly
    210                 215                 220

Val Ile Ala Glu Gln Ala Ile Ala Gln Val Arg Thr Val Tyr Ser Tyr
225                 230                 235                 240

Val Gly Glu Ser Lys Ala Leu Asn Ala Tyr Ser Asp Ala Ile Gln Tyr
                245                 250                 255

Thr Leu Lys Leu Gly Tyr Lys Ala Gly Met Ala Lys Gly Leu Gly Leu
            260                 265                 270

Gly Cys Thr Tyr Gly Ile Ala Cys Met Ser Trp Ala Leu Val Phe Trp
        275                 280                 285

Tyr Ala Gly Val Phe Ile Arg Asn Gly Gln Thr Asp Gly Gly Lys Ala
    290                 295                 300

Phe Thr Ala Ile Phe Ser Ala Ile Val Gly Gly Met Ser Leu Gly Gln
305                 310                 315                 320
```

```
Ser Phe Ser Asn Leu Gly Ala Phe Ser Lys Gly Lys Ala Ala Gly Tyr
            325                 330                 335

Lys Leu Met Glu Ile Ile Asn Gln Arg Pro Thr Ile Ile Gln Asp Pro
            340                 345                 350

Leu Asp Gly Lys Cys Leu Asp Gln Val His Gly Asn Ile Glu Phe Lys
            355                 360                 365

Asp Val Thr Phe Ser Tyr Pro Ser Arg Pro Asp Val Met Ile Phe Arg
    370                 375                 380

Asn Phe Asn Ile Phe Phe Pro Ser Gly Lys Thr Val Ala Val Val Gly
385                 390                 395                 400

Gly Ser Gly Ser Gly Lys Ser Thr Val Val Ser Leu Ile Glu Arg Phe
                405                 410                 415

Tyr Asp Pro Asn Ser Gly Gln Ile Leu Leu Asp Gly Val Glu Ile Lys
            420                 425                 430

Thr Leu Gln Leu Lys Phe Leu Arg Glu Gln Ile Gly Leu Val Asn Gln
            435                 440                 445

Glu Pro Ala Leu Phe Ala Thr Thr Ile Leu Glu Asn Ile Leu Tyr Gly
    450                 455                 460

Lys Pro Asp Ala Thr Met Val Glu Val Glu Ala Ala Ser Ala Ala
465                 470                 475                 480

Asn Ala His Ser Phe Ile Thr Leu Leu Pro Lys Gly Tyr Asp Thr Gln
                485                 490                 495

Val Gly Glu Arg Gly Val Gln Leu Ser Gly Gly Gln Lys Gln Arg Ile
            500                 505                 510

Ala Ile Ala Arg Ala Met Leu Lys Asp Pro Lys Ile Leu Leu Leu Asp
            515                 520                 525

Glu Ala Thr Ser Ala Leu Asp Ala Ser Ser Glu Ser Ile Val Gln Glu
    530                 535                 540

Ala Leu Asp Arg Val Met Val Gly Arg Thr Thr Val Val Val Ala His
545                 550                 555                 560

Arg Leu Cys Thr Ile Arg Asn Val Asp Ser Ile Ala Val Ile Gln Gln
                565                 570                 575

Gly Gln Val Val Glu Thr Gly Thr His Glu Glu Leu Ile Ala Lys Ser
            580                 585                 590

Gly Ala Tyr Ala Ser Leu Ile Arg Phe Gln Glu Met Val Gly Thr Arg
            595                 600                 605

Asp Phe Ser Asn Pro Ser Thr Arg Arg Thr Arg Ser Thr Arg Leu Ser
    610                 615                 620

His Ser Leu Ser Thr Lys Ser Leu Ser Leu Arg Ser Gly Ser Leu Arg
625                 630                 635                 640

Asn Leu Ser Tyr Ser Tyr Ser Thr Gly Ala Asp Gly Arg Ile Glu Met
                645                 650                 655

Ile Ser Asn Ala Glu Thr Asp Arg Lys Thr Arg Ala Pro Glu Asn Tyr
            660                 665                 670

Phe Tyr Arg Leu Leu Lys Leu Asn Ser Pro Glu Trp Pro Tyr Ser Ile
            675                 680                 685

Met Gly Ala Val Gly Ser Ile Leu Ser Gly Phe Ile Gly Pro Thr Phe
    690                 695                 700

Ala Ile Val Met Ser Asn Met Ile Glu Val Phe Tyr Tyr Thr Asp Tyr
705                 710                 715                 720

Asp Ser Met Glu Arg Lys Thr Lys Glu Tyr Val Phe Ile Tyr Ile Gly
                725                 730                 735

Ala Gly Leu Tyr Ala Val Gly Ala Tyr Leu Ile Gln His Tyr Phe Phe
```

-continued

```
            740                 745                 750
Ser Ile Met Gly Glu Asn Leu Thr Thr Arg Val Arg Arg Met Met Leu
        755                 760                 765
Ser Ala Ile Leu Arg Asn Glu Val Gly Trp Phe Asp Glu Asp Glu His
        770                 775                 780
Asn Ser Ser Leu Ile Ala Ala Arg Leu Ala Thr Asp Ala Ala Asp Val
785                 790                 795                 800
Lys Ser Ala Ile Ala Glu Arg Ile Ser Val Ile Leu Gln Asn Met Thr
                805                 810                 815
Ser Leu Leu Thr Ser Phe Ile Val Ala Phe Ile Val Glu Trp Arg Val
        820                 825                 830
Ser Leu Leu Ile Leu Gly Thr Phe Pro Leu Leu Val Leu Ala Asn Phe
        835                 840                 845
Ala Gln Gln Leu Ser Leu Lys Gly Phe Ala Gly Asp Thr Ala Lys Ala
        850                 855                 860
His Ala Lys Thr Ser Met Ile Ala Gly Glu Gly Val Ser Asn Ile Arg
865                 870                 875                 880
Thr Val Ala Ala Phe Asn Ala Gln Ser Lys Ile Leu Ser Leu Phe Cys
                885                 890                 895
His Glu Leu Arg Val Pro Gln Lys Arg Ser Leu Ser Leu Tyr Arg Ser
                900                 905                 910
Gln Thr Ser Gly Phe Leu Phe Gly Leu Ser Gln Leu Ala Leu Tyr Gly
        915                 920                 925
Ser Glu Ala Leu Ile Leu Trp Tyr Gly Ala His Leu Val Ser Lys Gly
        930                 935                 940
Val Ser Thr Phe Ser Lys Val Ile Lys Val Phe Val Val Leu Val Ile
945                 950                 955                 960
Thr Ala Asn Ser Val Ala Glu Thr Val Ser Leu Ala Pro Glu Ile Ile
                965                 970                 975
Arg Gly Gly Glu Ala Val Gly Ser Val Phe Ser Val Leu Asp Arg Gln
                980                 985                 990
Thr Arg Ile Asp Pro Asp Asp Ala Asp Ala Asp Pro Val Glu Thr Ile
        995                 1000                1005
Arg Gly Asp Ile Glu Phe Arg His Val Asp Phe Ala Tyr Pro Ser Arg
        1010                1015                1020
Pro Asp Val Met Val Phe Arg Asp Phe Asn Leu Arg Ile Arg Ala Gly
1025                1030                1035                1040
His Ser Gln Ala Leu Val Gly Ala Ser Gly Ser Gly Lys Ser Ser Val
                1045                1050                1055
Ile Ala Met Ile Glu Arg Phe Tyr Asp Leu Leu Ala Gly Lys Val Met
                1060                1065                1070
Ile Asp Gly Lys Asp Ile Arg Arg Leu Asn Leu Lys Ser Leu Arg Leu
        1075                1080                1085
Lys Ile Gly Leu Val Gln Gln Glu Pro Ala Leu Phe Ala Ala Thr Ile
        1090                1095                1100
Phe Asp Asn Ile Ala Tyr Gly Lys Asp Gly Ala Thr Glu Ser Glu Val
1105                1110                1115                1120
Ile Asp Ala Ala Arg Ala Ala Asn Ala His Gly Phe Ile Ser Gly Leu
                1125                1130                1135
Pro Glu Gly Tyr Lys Thr Pro Val Gly Glu Arg Gly Val Gln Leu Ser
                1140                1145                1150
Gly Gly Gln Lys Gln Arg Ile Ala Ile Ala Arg Ala Val Leu Lys Asn
        1155                1160                1165
```

```
Pro Thr Val Leu Leu Asp Glu Ala Thr Ser Ala Leu Asp Ala Glu
    1170                1175                1180
Ser Glu Cys Val Leu Gln Glu Ala Leu Glu Arg Leu Met Arg Gly Arg
1185            1190                1195                1200
Thr Thr Val Val Ala His Arg Leu Ser Thr Ile Arg Gly Val Asp
                1205                1210                1215
Cys Ile Gly Val Ile Gln Asp Gly Arg Ile Val Glu Gln Gly Ser His
            1220                1225                1230
Ser Glu Leu Val Ser Arg Pro Glu Gly Ala Tyr Ser Arg Leu Leu Gln
            1235                1240                1245
Leu Gln Thr His Arg Ile
    1250

<210> SEQ ID NO 3
<211> LENGTH: 1280
<212> TYPE: PRT
<213> ORGANISM: Homo sapiens
<300> PUBLICATION INFORMATION:
<308> DATABASE ACCESSION NUMBER: Genbank P08183
<309> DATABASE ENTRY DATE: 1997-11-01

<400> SEQUENCE: 3

Met Asp Leu Glu Gly Asp Arg Asn Gly Gly Ala Lys Lys Lys Asn Phe
1               5                   10                  15
Phe Lys Leu Asn Asn Lys Ser Glu Lys Asp Lys Lys Glu Lys Lys Pro
                20                  25                  30
Thr Val Ser Val Phe Ser Met Phe Arg Tyr Ser Asn Trp Leu Asp Lys
            35                  40                  45
Leu Tyr Met Val Val Gly Thr Leu Ala Ala Ile Ile His Gly Ala Gly
        50                  55                  60
Leu Pro Leu Met Met Leu Val Phe Gly Glu Met Thr Asp Ile Phe Ala
65                  70                  75                  80
Asn Ala Gly Asn Leu Glu Asp Leu Met Ser Asn Ile Thr Asn Arg Ser
                85                  90                  95
Asp Ile Asn Asp Thr Gly Phe Phe Met Asn Leu Glu Glu Asp Met Thr
            100                 105                 110
Arg Tyr Ala Tyr Tyr Tyr Ser Gly Ile Gly Ala Gly Val Leu Val Ala
        115                 120                 125
Ala Tyr Ile Gln Val Ser Phe Trp Cys Leu Ala Ala Gly Arg Gln Ile
    130                 135                 140
His Lys Ile Arg Lys Gln Phe Phe His Ala Ile Met Arg Gln Glu Ile
145                 150                 155                 160
Gly Trp Phe Asp Val His Asp Val Gly Glu Leu Asn Thr Arg Leu Thr
                165                 170                 175
Asp Asp Val Ser Lys Ile Asn Glu Val Ile Gly Asp Lys Ile Gly Met
            180                 185                 190
Phe Phe Gln Ser Met Ala Thr Phe Phe Thr Gly Phe Ile Val Gly Phe
        195                 200                 205
Thr Arg Gly Trp Lys Leu Thr Leu Val Ile Leu Ala Ile Ser Pro Val
    210                 215                 220
Leu Gly Leu Ser Ala Ala Val Trp Ala Lys Ile Leu Ser Ser Phe Thr
225                 230                 235                 240
Asp Lys Glu Leu Leu Ala Tyr Ala Lys Ala Gly Ala Val Ala Glu Glu
                245                 250                 255
Val Leu Ala Ala Ile Arg Thr Val Ile Ala Phe Gly Gly Gln Lys Lys
```

-continued

```
            260                 265                 270
Glu Leu Glu Arg Tyr Asn Lys Asn Leu Glu Glu Ala Lys Arg Ile Gly
            275                 280                 285

Ile Lys Lys Ala Ile Thr Ala Asn Ile Ser Ile Gly Ala Ala Phe Leu
290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
            355                 360                 365

Ile Asp Asn Lys Pro Ser Ile Asp Ser Tyr Ser Lys Ser Gly His Lys
            370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
            435                 440                 445

Gly Met Val Ser Val Asp Gly Gln Asp Ile Arg Thr Ile Asn Val Arg
            450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
                500                 505                 510

Ile Met Lys Leu Pro His Lys Phe Asp Thr Leu Val Gly Glu Arg Gly
            515                 520                 525

Ala Gln Leu Ser Gly Gly Gln Lys Gln Arg Ile Ala Ile Ala Arg Ala
            530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
                580                 585                 590

Arg Asn Ala Asp Val Ile Ala Gly Phe Asp Asp Gly Val Ile Val Glu
            595                 600                 605

Lys Gly Asn His Asp Glu Leu Met Lys Glu Lys Gly Ile Tyr Phe Lys
            610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
            660                 665                 670

Arg Gly Ser Gln Ala Gln Asp Arg Lys Leu Ser Thr Lys Glu Ala Leu
            675                 680                 685
```

-continued

```
Asp Glu Ser Ile Pro Pro Val Ser Phe Trp Arg Ile Met Lys Leu Asn
    690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
            740                 745                 750

Asn Leu Phe Ser Leu Leu Phe Leu Ala Leu Gly Ile Ile Ser Phe Ile
        755                 760                 765

Thr Phe Phe Leu Gln Gly Phe Thr Phe Gly Lys Ala Gly Glu Ile Leu
    770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
            820                 825                 830

Leu Ala Val Ile Thr Gln Asn Ile Ala Asn Leu Gly Thr Gly Ile Ile
        835                 840                 845

Ile Ser Phe Ile Tyr Gly Trp Gln Leu Thr Leu Leu Leu Leu Ala Ile
    850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
            900                 905                 910

Glu Gln Lys Phe Glu His Met Tyr Ala Gln Ser Leu Gln Val Pro Tyr
        915                 920                 925

Arg Asn Ser Leu Arg Lys Ala His Ile Phe Gly Ile Thr Phe Ser Phe
    930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Phe Gly Ala Met Ala Val Gly Gln Val Ser
            980                 985                 990

Ser Phe Ala Pro Asp Tyr Ala Lys Ala Lys Ile Ser Ala Ala His Ile
        995                 1000                1005

Ile Met Ile Ile Glu Lys Thr Pro Leu Ile Asp Ser Tyr Ser Thr Glu
    1010                1015                1020

Gly Leu Met Pro Asn Thr Leu Glu Gly Asn Val Thr Phe Gly Glu Val
1025                1030                1035                1040

Val Phe Asn Tyr Pro Thr Arg Pro Asp Ile Pro Val Leu Gln Gly Leu
                1045                1050                1055

Ser Leu Glu Val Lys Lys Gly Gln Thr Leu Ala Leu Val Gly Ser Ser
            1060                1065                1070

Gly Cys Gly Lys Ser Thr Val Val Gln Leu Leu Glu Arg Phe Tyr Asp
        1075                1080                1085

Pro Leu Ala Gly Lys Val Leu Leu Asp Gly Lys Glu Ile Lys Arg Leu
    1090                1095                1100
```

-continued

```
Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
                1125                1130                1135

Ser Arg Val Val Ser Gln Glu Glu Ile Val Arg Ala Ala Lys Glu Ala
            1140                1145                1150

Asn Ile His Ala Phe Ile Glu Ser Leu Pro Asn Lys Tyr Ser Thr Lys
        1155                1160                1165

Val Gly Asp Lys Gly Thr Gln Leu Ser Gly Gly Gln Lys Gln Arg Ile
    1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
                1205                1210                1215

Ala Leu Asp Lys Ala Arg Glu Gly Arg Thr Cys Ile Val Ile Ala His
            1220                1225                1230

Arg Leu Ser Thr Ile Gln Asn Ala Asp Leu Ile Val Val Phe Gln Asn
        1235                1240                1245

Gly Arg Val Lys Glu His Gly Thr His Gln Gln Leu Leu Ala Gln Lys
    1250                1255                1260

Gly Ile Tyr Phe Ser Met Val Ser Val Gln Ala Gly Thr Lys Arg Gln
1265                1270                1275                1280
```

<210> SEQ ID NO 4
<211> LENGTH: 1175
<212> TYPE: PRT
<213> ORGANISM: Mus musculus
<300> PUBLICATION INFORMATION:
<308> DATABASE ACCESSION NUMBER: Genbank P06795
<309> DATABASE ENTRY DATE: 1998-07-15

<400> SEQUENCE: 4

```
Ser Asn Ser Ser Leu Glu Glu Glu Met Ala Ile Tyr Ala Tyr Tyr Tyr
  1               5                  10                  15

Thr Gly Ile Gly Ala Gly Val Leu Ile Val Ala Tyr Ile Gln Val Ser
             20                  25                  30

Leu Trp Cys Leu Ala Ala Gly Arg Gln Ile His Lys Ile Arg Gln Lys
         35                  40                  45

Phe Phe His Ala Ile Met Asn Gln Glu Ile Gly Trp Phe Asp Val His
     50                  55                  60

Asp Val Gly Glu Leu Asn Thr Arg Leu Thr Asp Asp Val Ser Lys Ile
 65                  70                  75                  80

Asn Asp Gly Ile Gly Asp Lys Ile Gly Met Phe Phe Gln Ser Ile Thr
                 85                  90                  95

Thr Phe Leu Ala Gly Phe Ile Ile Gly Phe Ile Ser Gly Trp Lys Leu
            100                 105                 110

Thr Leu Val Ile Leu Ala Val Ser Pro Leu Ile Gly Leu Ser Ser Ala
        115                 120                 125

Leu Trp Ala Lys Val Leu Thr Ser Phe Thr Asn Lys Glu Leu Gln Ala
    130                 135                 140

Tyr Ala Lys Ala Gly Ala Val Ala Glu Glu Val Leu Ala Ala Ile Arg
145                 150                 155                 160

Thr Val Ile Ala Phe Gly Gly Gln Gln Lys Glu Leu Glu Arg Tyr Asn
                165                 170                 175

Lys Asn Leu Glu Glu Ala Lys Asn Val Gly Ile Lys Lys Ala Ile Thr
            180                 185                 190
```

-continued

```
Ala Ser Ile Ser Ile Gly Ile Ala Tyr Leu Leu Val Tyr Ala Ser Tyr
            195                 200                 205

Ala Leu Ala Phe Trp Tyr Gly Thr Ser Leu Val Leu Ser Asn Glu Tyr
    210                 215                 220

Ser Ile Gly Glu Val Leu Thr Val Phe Phe Ser Ile Leu Leu Gly Thr
225                 230                 235                 240

Phe Ser Ile Gly His Leu Ala Pro Asn Ile Glu Ala Phe Ala Asn Ala
            245                 250                 255

Arg Gly Ala Ala Phe Glu Ile Phe Lys Ile Ile Asp Asn Glu Pro Ser
            260                 265                 270

Ile Asp Ser Phe Ser Thr Lys Gly Tyr Lys Pro Asp Ser Ile Met Gly
    275                 280                 285

Asn Leu Glu Phe Lys Asn Val His Phe Asn Tyr Pro Ser Arg Ser Glu
    290                 295                 300

Val Gln Ile Leu Lys Gly Leu Asn Leu Lys Val Lys Ser Gly Gln Thr
305                 310                 315                 320

Val Ala Leu Val Gly Asn Ser Gly Cys Gly Lys Ser Thr Thr Val Gln
            325                 330                 335

Leu Met Gln Arg Leu Tyr Asp Pro Leu Glu Gly Val Val Ser Ile Asp
            340                 345                 350

Gly Gln Asp Ile Arg Thr Ile Asn Val Arg Tyr Leu Arg Glu Ile Ile
            355                 360                 365

Gly Val Val Ser Gln Glu Pro Val Leu Phe Ala Thr Thr Ile Ala Glu
    370                 375                 380

Asn Ile Arg Tyr Gly Arg Glu Asp Val Thr Met Asp Glu Ile Glu Lys
385                 390                 395                 400

Ala Val Lys Glu Ala Asn Ala Tyr Asp Phe Ile Met Lys Leu Pro His
            405                 410                 415

Gln Phe Asp Thr Leu Val Gly Glu Arg Gly Ala Gln Leu Ser Gly Gly
            420                 425                 430

Gln Lys Gln Arg Ile Ala Ile Ala Arg Ala Leu Val Arg Asn Pro Lys
    435                 440                 445

Ile Leu Leu Leu Asp Glu Ala Thr Ser Ala Leu Asp Thr Glu Ser Glu
    450                 455                 460

Ala Val Val Gln Ala Ala Leu Asp Lys Ala Arg Glu Gly Arg Thr Thr
465                 470                 475                 480

Ile Val Ile Ala His Arg Leu Ser Thr Val Arg Asn Ala Asp Val Ile
            485                 490                 495

Ala Gly Phe Asp Gly Gly Val Ile Val Glu Gln Gly Asn His Asp Glu
            500                 505                 510

Leu Met Arg Glu Lys Gly Ile Tyr Phe Lys Leu Val Met Thr Gln Thr
    515                 520                 525

Arg Gly Asn Glu Ile Glu Pro Gly Asn Asn Ala Tyr Gly Ser Gln Ser
    530                 535                 540

Asp Thr Asp Ala Ser Glu Leu Thr Ser Glu Glu Ser Lys Ser Pro Leu
545                 550                 555                 560

Ile Arg Arg Ser Ile Tyr Arg Ser Val His Arg Lys Gln Asp Gln Glu
            565                 570                 575

Arg Arg Leu Ser Met Lys Glu Ala Val Asp Glu Asp Val Pro Leu Val
            580                 585                 590

Ser Phe Trp Arg Ile Leu Asn Leu Asn Leu Ser Glu Trp Pro Tyr Leu
    595                 600                 605
```

-continued

```
Leu Val Gly Val Leu Cys Ala Val Ile Asn Gly Cys Ile Gln Pro Val
    610                 615                 620
Phe Ala Ile Val Phe Ser Arg Ile Val Gly Val Phe Ser Arg Asp Asp
625                 630                 635                 640
Asp His Glu Thr Lys Arg Gln Asn Cys Asn Leu Phe Ser Leu Phe Phe
                645                 650                 655
Leu Val Met Gly Leu Ile Ser Phe Val Thr Tyr Phe Phe Gln Gly Phe
            660                 665                 670
Thr Phe Gly Lys Ala Gly Glu Ile Leu Thr Lys Arg Val Arg Tyr Met
        675                 680                 685
Val Phe Lys Ser Met Leu Arg Gln Asp Ile Ser Trp Phe Asp Asp His
    690                 695                 700
Lys Asn Ser Thr Gly Ser Leu Thr Thr Arg Leu Ala Ser Asp Ala Ser
705                 710                 715                 720
Ser Val Lys Gly Ala Met Gly Ala Arg Leu Ala Val Val Thr Gln Asn
                725                 730                 735
Val Ala Asn Leu Gly Thr Gly Val Ile Leu Ser Leu Val Tyr Gly Trp
            740                 745                 750
Gln Leu Thr Leu Leu Val Val Ile Pro Leu Ile Val Leu Gly
        755                 760                 765
Gly Ile Ile Glu Met Lys Leu Leu Ser Gly Gln Ala Leu Lys Asp Lys
    770                 775                 780
Lys Gln Leu Glu Ile Ser Gly Lys Ile Ala Thr Glu Ala Ile Glu Asn
785                 790                 795                 800
Phe Arg Thr Ile Val Ser Leu Thr Arg Glu Gln Lys Phe Glu Thr Met
                805                 810                 815
Tyr Ala Gln Ser Leu Gln Val Pro Tyr Arg Asn Ala Met Lys Lys Ala
            820                 825                 830
His Val Phe Gly Ile Thr Phe Ser Phe Thr Gln Ala Met Met Tyr Phe
        835                 840                 845
Ser Tyr Ala Ala Cys Phe Arg Phe Gly Ala Tyr Leu Val Ala Gln Gln
    850                 855                 860
Leu Met Thr Phe Glu Asn Val Met Leu Val Phe Ser Ala Val Val Phe
865                 870                 875                 880
Gly Ala Met Ala Ala Gly Asn Thr Ser Ser Phe Ala Pro Asp Tyr Ala
                885                 890                 895
Lys Ala Lys Val Ser Ala Ser His Ile Ile Arg Ile Ile Glu Lys Thr
            900                 905                 910
Pro Glu Ile Asp Ser Tyr Ser Thr Glu Gly Leu Lys Pro Thr Leu Leu
        915                 920                 925
Glu Gly Asn Val Lys Phe Asn Gly Val Gln Phe Asn Tyr Pro Thr Arg
    930                 935                 940
Pro Asn Ile Pro Val Leu Gln Gly Leu Ser Leu Glu Val Lys Lys Gly
945                 950                 955                 960
Gln Thr Leu Ala Leu Val Gly Ser Ser Gly Cys Gly Lys Ser Thr Val
                965                 970                 975
Val Gln Leu Leu Glu Arg Phe Tyr Asp Pro Met Ala Gly Ser Val Phe
            980                 985                 990
Leu Asp Gly Lys Glu Ile Lys Gln Leu Asn Val Gln Trp Leu Arg Ala
        995                 1000                1005
His Leu Gly Ile Val Ser Gln Glu Pro Ile Leu Phe Asp Cys Ser Ile
    1010                1015                1020
Ala Glu Asn Ile Ala Tyr Gly Asp Asn Ser Arg Ala Val Ser His Glu
```

-continued

```
                 1025                1030                1035                1040
Glu Ile Val Arg Ala Ala Lys Glu Ala Asn Ile His Gln Phe Ile Asp
                     1045                1050                1055
Ser Leu Pro Asp Lys Tyr Asn Thr Arg Val Gly Asp Lys Gly Thr Gln
                     1060                1065                1070
Leu Ser Gly Gly Gln Lys Gln Arg Ile Ala Ile Ala Arg Ala Leu Val
                     1075                1080                1085
Arg Gln Pro His Ile Leu Leu Leu Asp Glu Ala Thr Ser Ala Leu Asp
         1090                1095                1100
Thr Glu Ser Glu Lys Val Val Gln Glu Ala Leu Asp Lys Ala Arg Glu
1105                1110                1115                1120
Gly Arg Thr Cys Ile Val Ile Ala His Arg Leu Ser Thr Ile Gln Asn
                     1125                1130                1135
Ala Asp Leu Ile Val Val Ile Glu Asn Gly Lys Val Lys Glu His Gly
                     1140                1145                1150
Thr His Gln Gln Leu Leu Ala Gln Lys Gly Ile Tyr Phe Ser Met Val
                     1155                1160                1165
Gln Ala Gly Ala Lys Arg Ser
                     1170                1175
```

<210> SEQ ID NO 5
<211> LENGTH: 1066
<212> TYPE: PRT
<213> ORGANISM: Homo sapiens
<300> PUBLICATION INFORMATION:
<308> DATABASE ACCESSION NUMBER: Genbank P21439
<309> DATABASE ENTRY DATE: 1998-07-15

<400> SEQUENCE: 5

```
Trp Lys Leu Thr Leu Val Ile Met Ala Ile Ser Pro Ile Leu Gly Leu
  1               5                  10                  15
Ser Ala Ala Val Trp Ala Lys Ile Leu Ser Ala Phe Ser Asp Lys Glu
                 20                  25                  30
Leu Ala Ala Tyr Ala Lys Ala Gly Ala Val Ala Glu Glu Ala Leu Gly
             35                  40                  45
Ala Ile Arg Thr Val Ile Ala Phe Gly Gly Gln Asn Lys Glu Leu Glu
         50                  55                  60
Arg Tyr Gln Lys His Leu Glu Asn Ala Lys Glu Ile Gly Ile Lys Lys
     65                  70                  75                  80
Ala Ile Ser Ala Asn Ile Ser Met Gly Ile Ala Phe Leu Leu Ile Tyr
                 85                  90                  95
Ala Ser Tyr Ala Leu Ala Phe Trp Tyr Gly Ser Thr Leu Val Ile Ser
                100                 105                 110
Lys Glu Tyr Thr Ile Gly Asn Ala Met Thr Val Phe Phe Ser Ile Leu
             115                 120                 125
Ile Gly Ala Phe Ser Val Gly Gln Ala Ala Pro Cys Ile Asp Ala Phe
         130                 135                 140
Ala Asn Ala Arg Gly Ala Ala Tyr Val Ile Phe Asp Ile Ile Asp Asn
145                 150                 155                 160
Asn Pro Lys Ile Asp Ser Phe Ser Glu Arg Gly His Lys Pro Asp Ser
                165                 170                 175
Ile Lys Gly Asn Leu Glu Phe Asn Asp Val His Phe Ser Tyr Pro Ser
                180                 185                 190
Arg Ala Asn Val Lys Ile Leu Lys Gly Leu Asn Leu Lys Val Gln Ser
            195                 200                 205
```

-continued

Gly Gln Thr Val Ala Leu Val Gly Ser Ser Gly Cys Gly Lys Ser Thr
210                215                220

Thr Val Gln Leu Ile Gln Arg Leu Tyr Asp Pro Asp Glu Gly Thr Ile
225                230                235                240

Asn Ile Asp Gly Gln Asp Ile Arg Asn Phe Asn Val Asn Tyr Leu Arg
                245                250                255

Glu Ile Ile Gly Val Val Ser Gln Glu Pro Val Leu Phe Ser Thr Thr
            260                265                270

Ile Ala Glu Asn Ile Cys Tyr Gly Arg Gly Asn Val Thr Met Asp Glu
        275                280                285

Ile Lys Lys Ala Val Lys Glu Ala Asn Ala Tyr Glu Phe Ile Met Lys
290                295                300

Leu Pro Gln Lys Phe Asp Thr Leu Val Gly Glu Arg Gly Ala Gln Leu
305                310                315                320

Ser Gly Gly Gln Lys Gln Arg Ile Ala Ile Ala Arg Ala Leu Val Arg
            325                330                335

Asn Pro Lys Ile Leu Leu Leu Asp Glu Ala Thr Ser Ala Leu Asp Thr
            340                345                350

Glu Ser Glu Ala Glu Val Gln Ala Ala Leu Asp Lys Ala Arg Glu Gly
        355                360                365

Arg Thr Thr Ile Val Ile Ala His Arg Leu Ser Thr Val Arg Asn Ala
370                375                380

Asp Val Ile Ala Gly Phe Glu Asp Gly Val Ile Val Glu Gln Gly Ser
385                390                395                400

His Ser Glu Leu Met Lys Lys Glu Gly Val Tyr Phe Lys Leu Val Asn
            405                410                415

Met Gln Thr Ser Gly Ser Gln Ile Gln Ser Glu Glu Phe Glu Leu Asn
            420                425                430

Asp Glu Lys Ala Ala Thr Arg Met Ala Pro Asn Gly Trp Lys Ser Arg
        435                440                445

Leu Phe Arg His Ser Thr Gln Lys Asn Leu Lys Asn Ser Gln Met Cys
450                455                460

Gln Lys Ser Leu Asp Val Glu Thr Asp Gly Leu Glu Ala Asn Val Pro
465                470                475                480

Pro Val Ser Phe Leu Lys Val Leu Lys Leu Asn Lys Thr Glu Trp Pro
            485                490                495

Tyr Phe Val Val Gly Thr Val Cys Ala Ile Ala Asn Gly Gly Leu Gln
            500                505                510

Pro Ala Phe Ser Val Ile Phe Ser Glu Ile Ile Ala Ile Phe Gly Pro
        515                520                525

Gly Asp Asp Ala Val Lys Gln Gln Lys Cys Asn Ile Phe Ser Leu Ile
530                535                540

Phe Leu Phe Leu Gly Ile Ile Ser Phe Thr Phe Phe Leu Gln Gly
545                550                555                560

Phe Thr Phe Gly Lys Ala Gly Glu Ile Leu Thr Arg Arg Leu Arg Ser
            565                570                575

Met Ala Phe Lys Ala Met Leu Arg Gln Asp Met Ser Trp Phe Asp Asp
            580                585                590

His Lys Asn Ser Thr Gly Ala Leu Ser Thr Arg Leu Ala Thr Asp Ala
        595                600                605

Ala Gln Val Gln Gly Ala Thr Gly Thr Arg Leu Ala Leu Ile Ala Gln
610                615                620

Asn Ile Ala Asn Leu Gly Thr Gly Ile Ile Ile Ser Phe Ile Tyr Gly

-continued

```
            625                 630                 635                 640
Trp Gln Leu Thr Leu Leu Leu Ala Val Val Pro Ile Ile Ala Val
                645                 650                 655
Ser Gly Ile Val Glu Met Lys Leu Leu Ala Gly Asn Ala Lys Arg Asp
                660                 665                 670
Lys Lys Glu Leu Glu Ala Ala Gly Lys Ile Ala Thr Glu Ala Ile Glu
                675                 680                 685
Asn Ile Arg Thr Val Val Ser Leu Thr Gln Glu Arg Lys Phe Glu Ser
            690                 695                 700
Met Tyr Val Glu Lys Leu Tyr Gly Pro Tyr Arg Asn Ser Val Gln Lys
705                 710                 715                 720
Ala His Ile Tyr Gly Ile Thr Phe Ser Ile Ser Gln Ala Phe Met Tyr
                725                 730                 735
Phe Ser Tyr Ala Gly Cys Phe Arg Phe Gly Ala Tyr Leu Ile Val Asn
                740                 745                 750
Gly His Met Arg Phe Arg Asp Val Ile Leu Val Phe Ser Ala Ile Val
                755                 760                 765
Phe Gly Ala Val Ala Leu Gly His Ala Ser Ser Phe Ala Pro Asp Tyr
                770                 775                 780
Ala Lys Ala Lys Leu Ser Ala Ala His Leu Phe Met Leu Phe Glu Arg
785                 790                 795                 800
Gln Pro Leu Ile Asp Ser Tyr Ser Glu Glu Gly Leu Lys Pro Asp Lys
                805                 810                 815
Phe Glu Gly Asn Ile Thr Phe Asn Glu Val Val Phe Asn Tyr Pro Thr
                820                 825                 830
Arg Ala Asn Val Pro Val Leu Gln Gly Leu Ser Leu Glu Val Lys Lys
                835                 840                 845
Gly Gln Thr Leu Ala Leu Val Gly Ser Ser Gly Cys Gly Lys Ser Thr
            850                 855                 860
Val Val Gln Leu Leu Glu Arg Phe Tyr Asp Pro Leu Ala Gly Thr Val
865                 870                 875                 880
Leu Leu Asp Gly Gln Glu Ala Lys Lys Leu Asn Val Gln Trp Leu Arg
                885                 890                 895
Ala Gln Leu Gly Ile Val Ser Gln Glu Pro Ile Leu Phe Asp Cys Ser
                900                 905                 910
Ile Ala Glu Asn Ile Ala Tyr Gly Asp Asn Ser Arg Val Val Ser Gln
            915                 920                 925
Asp Glu Ile Val Ser Ala Ala Lys Ala Ala Asn Ile His Pro Phe Ile
            930                 935                 940
Glu Thr Leu Pro His Lys Tyr Glu Thr Arg Val Gly Asp Lys Gly Thr
945                 950                 955                 960
Gln Leu Ser Gly Gly Gln Lys Gln Arg Ile Ala Ile Ala Arg Ala Leu
                965                 970                 975
Ile Arg Gln Pro Gln Ile Leu Leu Leu Asp Glu Ala Thr Ser Ala Leu
                980                 985                 990
Asp Thr Glu Ser Glu Lys Val Val Gln Glu Ala Leu Asp Lys Ala Arg
            995                 1000                1005
Glu Gly Arg Thr Cys Ile Val Ile Ala His Arg Leu Ser Thr Ile Gln
            1010                1015                1020
Asn Ala Asp Leu Ile Val Val Phe Gln Asn Gly Arg Val Lys Glu His
1025                1030                1035                1040
Gly Thr His Gln Gln Leu Leu Ala Gln Lys Gly Ile Tyr Phe Ser Met
                1045                1050                1055
```

```
Val Ser Val Gln Ala Gly Thr Gln Asn Leu
            1060                1065

<210> SEQ ID NO 6
<211> LENGTH: 1266
<212> TYPE: PRT
<213> ORGANISM: Mus musculus
<300> PUBLICATION INFORMATION:
<308> DATABASE ACCESSION NUMBER: Genbank P21440
<309> DATABASE ENTRY DATE: 1997-11-01

<400> SEQUENCE: 6

Trp Lys Leu Thr Leu Val Ile Met Ala Ile Ser Pro Ile Leu Gly Leu
 1               5                  10                  15

Ser Thr Ala Val Trp Ala Lys Ile Leu Ser Thr Phe Ser Asp Lys Glu
            20                  25                  30

Leu Ala Ala Tyr Ala Lys Ala Gly Ala Val Ala Glu Glu Ala Pro Gly
        35                  40                  45

Ala Ile Arg Thr Val Ile Ala Phe Gly Gly Gln Asn Lys Glu Leu Glu
    50                  55                  60

Arg Tyr Gln Lys His Leu Glu Asn Ala Lys Lys Ile Gly Ile Lys Lys
65                  70                  75                  80

Ala Ile Ser Ala Asn Ile Ser Met Gly Ile Ala Phe Leu Leu Ile Tyr
                85                  90                  95

Ala Ser Tyr Ala Leu Ala Phe Trp Tyr Gly Ser Thr Leu Val Ile Ser
            100                 105                 110

Lys Glu Tyr Thr Ile Gly Asn Ala Met Thr Val Phe Phe Ser Ile Leu
        115                 120                 125

Ile Gly Ala Phe Ser Val Gly Gln Ala Ala Pro Cys Ile Asp Ala Phe
    130                 135                 140

Ala Asn Ala Arg Gly Ala Ala Tyr Val Ile Phe Asp Ile Ile Asp Asn
145                 150                 155                 160

Asn Pro Lys Ile Asp Ser Phe Ser Glu Arg Gly His Lys Pro Asp Asn
                165                 170                 175

Ile Lys Gly Asn Leu Glu Phe Ser Asp Val His Phe Ser Tyr Pro Ser
            180                 185                 190

Arg Ala Asn Ile Lys Ile Leu Lys Gly Leu Asn Leu Lys Val Lys Ser
        195                 200                 205

Gly Gln Thr Val Ala Leu Val Gly Asn Ser Gly Cys Gly Lys Ser Thr
    210                 215                 220

Thr Val Gln Leu Leu Gln Arg Leu Tyr Asp Pro Thr Glu Gly Lys Ile
225                 230                 235                 240

Ser Ile Asp Gly Gln Asp Ile Arg Asn Phe Asn Val Arg Cys Leu Arg
                245                 250                 255

Glu Ile Ile Gly Val Val Ser Gln Glu Pro Val Leu Phe Ser Thr Thr
            260                 265                 270

Ile Ala Glu Asn Ile Arg Tyr Gly Arg Gly Asn Val Thr Met Asp Glu
        275                 280                 285

Ile Glu Lys Ala Val Lys Glu Ala Asn Ala Tyr Asp Phe Ile Met Lys
    290                 295                 300

Leu Pro Gln Lys Phe Asp Thr Leu Val Gly Asp Arg Gly Ala Gln Leu
305                 310                 315                 320

Ser Gly Gly Gln Lys Gln Arg Ile Ala Ile Ala Arg Ala Leu Val Arg
                325                 330                 335

Asn Pro Lys Ile Leu Leu Leu Asp Glu Ala Thr Ser Ala Leu Asp Thr
```

```
              340             345             350
Glu Ser Glu Ala Glu Val Gln Ala Ala Leu Asp Lys Ala Arg Glu Gly
            355                 360                 365
Arg Thr Thr Ile Val Ile Ala His Arg Leu Ser Thr Ile Arg Asn Ala
        370                 375                 380
Asp Val Ile Ala Gly Phe Glu Asp Gly Val Ile Val Glu Gln Gly Ser
385                 390                 395                 400
His Ser Glu Leu Met Lys Lys Glu Gly Ile Tyr Phe Arg Leu Val Asn
                405                 410                 415
Met Gln Thr Ala Gly Ser Gln Ile Leu Ser Glu Glu Phe Glu Ala Arg
            420                 425                 430
Ala Leu Val Arg Asn Pro Lys Ile Leu Leu Leu Asp Glu Ala Thr Ser
            435                 440                 445
Ala Leu Asp Thr Glu Ser Glu Ala Val Val Gln Val Ala Leu Asp Lys
        450                 455                 460
Ala Arg Lys Gly Arg Thr Thr Ile Val Ile Ala His Arg Leu Ser Thr
465                 470                 475                 480
Val Arg Asn Ala Asp Val Ile Ala Gly Phe Asp Asp Gly Val Ile Val
                485                 490                 495
Glu Lys Gly Asn His Asp Glu Leu Met Lys Glu Lys Gly Ile Tyr Phe
            500                 505                 510
Lys Leu Val Thr Met Gln Thr Ala Gly Asn Glu Val Glu Leu Glu Asn
            515                 520                 525
Ala Ala Ala Arg Ala Leu Val Arg Asn Pro Lys Ile Leu Leu Leu Asp
        530                 535                 540
Glu Ala Thr Ser Ala Leu Asp Thr Glu Ser Glu Ala Val Val Gln Ala
545                 550                 555                 560
Ala Leu Asp Lys Ala Arg Glu Gly Arg Thr Thr Ile Val Ile Ala His
                565                 570                 575
Arg Leu Ser Thr Val Arg Asn Ala Asp Val Ile Ala Gly Phe Asp Gly
            580                 585                 590
Gly Val Ile Val Glu Gln Gly Asn His Asp Glu Leu Met Arg Glu Lys
            595                 600                 605
Gly Ile Tyr Phe Lys Leu Val Met Thr Gln Thr Arg Gly Asn Glu Ile
        610                 615                 620
Glu Pro Gly Asn Asn Ala Val Glu Leu Ser Asp Glu Lys Ala Ala Gly
625                 630                 635                 640
Asp Val Ala Pro Asn Gly Trp Lys Ala Arg Ile Phe Arg Asn Ser Thr
                645                 650                 655
Lys Lys Ser Leu Lys Ser Pro His Gln Asn Arg Leu Asp Glu Glu Thr
            660                 665                 670
Asn Glu Leu Asp Ala Asn Val Pro Pro Val Ser Phe Leu Lys Val Leu
            675                 680                 685
Lys Leu Asn Lys Thr Glu Trp Pro Tyr Phe Val Val Gly Thr Val Cys
        690                 695                 700
Ala Ile Ala Asn Gly Ala Leu Gln Pro Ala Phe Ser Ile Ile Leu Ser
705                 710                 715                 720
Glu Met Ile Ala Ile Phe Gly Pro Gly Asp Asp Ala Val Lys Gln Gln
                725                 730                 735
Lys Cys Asn Met Phe Ser Leu Val Phe Leu Gly Leu Gly Val Leu Ser
            740                 745                 750
Phe Phe Thr Phe Phe Leu Gln Gly Phe Thr Phe Gly Lys Ala Gly Glu
        755                 760                 765
```

-continued

```
Ile Leu Thr Thr Arg Leu Arg Ser Met Ala Phe Lys Ala Met Leu Arg
    770                 775                 780
Gln Asp Met Ser Trp Phe Asp Asp His Lys Asn Ser Thr Gly Ala Leu
785                 790                 795                 800
Ser Thr Arg Leu Ala Thr Asp Ala Ala Gln Val Gln Gly Ala Thr Gly
                805                 810                 815
Thr Lys Leu Ala Leu Ile Ala Gln Asn Thr Ala Asn Leu Gly Thr Gly
                820                 825                 830
Ile Ile Ile Ser Phe Ile Tyr Gly Trp Gln Leu Thr Leu Leu Leu Leu
                835                 840                 845
Ser Val Val Pro Phe Ile Ala Val Ala Gly Ile Val Glu Met Lys Met
    850                 855                 860
Leu Ala Gly Asn Ala Lys Arg Asp Lys Lys Glu Met Glu Ala Ala Gly
865                 870                 875                 880
Lys Ile Ala Thr Glu Ala Ile Glu Asn Ile Arg Thr Val Val Ser Leu
                885                 890                 895
Thr Gln Glu Arg Lys Phe Glu Ser Met Tyr Val Glu Lys Leu His Gly
                900                 905                 910
Pro Tyr Arg Asn Ser Val Arg Lys Ala His Ile Tyr Gly Ile Thr Phe
                915                 920                 925
Ser Ile Ser Gln Ala Phe Met Tyr Phe Ser Tyr Ala Gly Cys Phe Arg
    930                 935                 940
Phe Gly Ser Tyr Leu Ile Val Asn Gly His Met Arg Phe Lys Asp Val
945                 950                 955                 960
Ile Leu Val Phe Ser Ala Ile Val Leu Gly Ala Val Ala Leu Gly His
                965                 970                 975
Ala Ser Ser Phe Ala Pro Asp Tyr Ala Lys Ala Lys Leu Ser Ala Ala
                980                 985                 990
Tyr Leu Phe Ser Leu Phe Glu Arg Gln Pro Leu Ile Asp Ser Tyr Ser
                995                 1000                1005
Gly Glu Gly Leu Trp Pro Asp Lys Phe Glu Gly Ser Val Thr Phe Asn
    1010                1015                1020
Glu Val Val Phe Asn Tyr Pro Thr Arg Ala Asn Val Pro Val Leu Gln
1025                1030                1035                1040
Gly Leu Ser Leu Glu Val Lys Lys Gly Gln Thr Leu Ala Leu Val Gly
                1045                1050                1055
Ser Ser Gly Cys Gly Lys Ser Thr Val Val Gln Leu Leu Glu Arg Phe
                1060                1065                1070
Tyr Asp Pro Met Ala Gly Ser Val Leu Leu Asp Gly Gln Glu Ala Lys
                1075                1080                1085
Lys Leu Asn Val Gln Trp Leu Arg Ala Gln Leu Gly Ile Val Ser Gln
    1090                1095                1100
Glu Pro Ile Leu Phe Asp Cys Ser Ile Ala Glu Asn Ile Ala Tyr Gly
1105                1110                1115                1120
Asp Asn Ser Arg Val Val Pro His Asp Glu Ile Val Arg Ala Ala Lys
                1125                1130                1135
Glu Ala Asn Ile His Pro Phe Ile Glu Thr Leu Pro Gln Lys Tyr Asn
                1140                1145                1150
Thr Arg Val Gly Asp Lys Gly Thr Gln Leu Ser Gly Gly Gln Lys Gln
                1155                1160                1165
Arg Ile Ala Ile Ala Arg Ala Leu Ile Arg Gln Pro Arg Val Leu Leu
    1170                1175                1180
```

-continued

Leu Asp Glu Ala Thr Ser Ala Leu Asp Thr Glu Ser Glu Lys Val Val
1185                1190                1195                1200

Gln Glu Ala Leu Asp Lys Ala Arg Glu Gly Arg Thr Cys Ile Val Ile
            1205                1210                1215

Ala His Arg Leu Ser Thr Ile Gln Asn Ala Asp Leu Ile Val Val Ile
        1220                1225                1230

Glu Asn Gly Lys Val Lys Glu His Gly Thr His Gln Gln Leu Leu Ala
    1235                1240                1245

Gln Lys Gly Ile Tyr Phe Ser Met Val Asn Ile Gln Ala Gly Thr Gln
    1250                1255                1260

Asn Leu
1265

<210> SEQ ID NO 7
<211> LENGTH: 1207
<212> TYPE: PRT
<213> ORGANISM: Arabidopsis thaliana
<300> PUBLICATION INFORMATION:
<308> DATABASE ACCESSION NUMBER: Genbank A42150
<309> DATABASE ENTRY DATE: 1997-03-13

<400> SEQUENCE: 7

Glu Lys Met Met Glu Glu Val Leu Lys Tyr Ala Leu Tyr Phe Leu Val
1               5                   10                  15

Val Gly Ala Ala Ile Trp Ala Ser Ser Trp Ala Glu Ile Ser Cys Trp
            20                  25                  30

Met Trp Ser Gly Glu Arg Gln Thr Thr Lys Met Arg Ile Lys Tyr Leu
        35                  40                  45

Glu Ala Ala Leu Asn Gln Asp Ile Gln Phe Phe Asp Thr Glu Val Arg
    50                  55                  60

Thr Ser Asp Val Val Phe Ala Ile Asn Thr Asp Ala Val Met Val Gln
65                  70                  75                  80

Asp Ala Ile Ser Glu Lys Leu Gly Asn Phe Ile His Tyr Met Ala Thr
                85                  90                  95

Phe Val Ser Gly Phe Ile Val Gly Phe Thr Ala Val Trp Gln Leu Ala
            100                 105                 110

Leu Val Thr Leu Ala Val Val Pro Leu Ile Ala Val Ile Gly Gly Ile
        115                 120                 125

His Thr Thr Thr Leu Ser Lys Leu Ser Asn Lys Ser Gln Glu Ser Leu
130                 135                 140

Ser Gln Ala Gly Asn Ile Val Glu Gln Thr Val Val Gln Ile Arg Val
145                 150                 155                 160

Val Met Ala Phe Val Gly Glu Ser Arg Ala Ser Gln Ala Tyr Ser Ser
                165                 170                 175

Ala Leu Lys Ile Ala Gln Lys Leu Gly Tyr Lys Thr Gly Leu Ala Lys
            180                 185                 190

Gly Met Gly Leu Gly Ala Thr Tyr Phe Val Val Phe Cys Cys Tyr Ala
        195                 200                 205

Leu Leu Leu Trp Tyr Gly Gly Tyr Leu Val Arg His His Leu Thr Asn
    210                 215                 220

Gly Gly Leu Ala Ile Ala Thr Met Phe Ala Val Met Ile Gly Gly Leu
225                 230                 235                 240

Ala Leu Gly Gln Ser Ala Pro Ser Met Ala Ala Phe Ala Lys Ala Lys
                245                 250                 255

Val Ala Ala Ala Lys Ile Phe Arg Ile Ile Asp His Lys Pro Thr Ile
            260                 265                 270

-continued

Glu Arg Asn Ser Glu Ser Gly Val Glu Leu Asp Ser Val Thr Gly Leu
            275                 280                 285

Val Glu Leu Lys Asn Val Asp Phe Ser Tyr Pro Ser Arg Pro Asp Val
    290                 295                 300

Lys Ile Leu Asn Asn Phe Cys Leu Ser Val Pro Ala Gly Lys Thr Ile
305                 310                 315                 320

Ala Leu Val Gly Ser Ser Gly Ser Gly Lys Ser Thr Val Val Ser Leu
            325                 330                 335

Ile Glu Arg Phe Tyr Asp Pro Asn Ser Gly Gln Val Leu Leu Asp Gly
            340                 345                 350

Gln Asp Leu Lys Thr Leu Lys Leu Arg Trp Leu Arg Gln Gln Ile Gly
        355                 360                 365

Leu Val Ser Gln Glu Pro Ala Leu Phe Ala Thr Ser Ile Lys Glu Asn
    370                 375                 380

Ile Leu Leu Gly Arg Pro Asp Ala Asp Gln Val Glu Ile Glu Glu Ala
385                 390                 395                 400

Ala Arg Val Ala Asn Ala His Ser Phe Ile Ile Lys Leu Pro Asp Gly
            405                 410                 415

Phe Asp Thr Gln Val Gly Glu Arg Gly Leu Gln Leu Ser Gly Gly Gln
            420                 425                 430

Lys Gln Arg Ile Ala Ile Ala Arg Ala Met Leu Lys Asn Pro Ala Ile
        435                 440                 445

Leu Leu Leu Asp Glu Ala Thr Ser Ala Leu Asp Ser Glu Ser Glu Lys
    450                 455                 460

Leu Val Gln Glu Ala Leu Asp Arg Phe Met Ile Gly Arg Thr Thr Leu
465                 470                 475                 480

Ile Ile Ala His Arg Leu Ser Thr Ile Arg Lys Ala Asp Leu Val Ala
            485                 490                 495

Val Leu Gln Gln Gly Ser Val Ser Glu Ile Gly Thr His Asp Glu Leu
            500                 505                 510

Phe Ser Lys Gly Glu Asn Gly Val Tyr Ala Lys Leu Ile Lys Met Gln
        515                 520                 525

Glu Ala Ala His Glu Thr Ala Met Ser Asn Ala Arg Lys Ser Ser Ala
    530                 535                 540

Arg Pro Ser Ser Ala Arg Asn Ser Val Ser Ser Pro Ile Met Thr Arg
545                 550                 555                 560

Asn Ser Ser Tyr Gly Arg Ser Pro Tyr Ser Arg Arg Leu Ser Asp Phe
            565                 570                 575

Ser Thr Ser Asp Phe Ser Leu Ser Ile Asp Ala Ser Ser Tyr Pro Asn
            580                 585                 590

Tyr Arg Asn Glu Lys Leu Ala Phe Lys Asp Gln Ala Asn Ser Phe Trp
        595                 600                 605

Arg Leu Ala Lys Met Asn Ser Pro Glu Trp Lys Tyr Ala Leu Leu Gly
    610                 615                 620

Ser Val Gly Ser Val Ile Cys Gly Ser Leu Ser Ala Phe Phe Ala Tyr
625                 630                 635                 640

Val Leu Ser Ala Val Leu Ser Val Tyr Tyr Asn Pro Asp His Glu Tyr
            645                 650                 655

Met Ile Lys Gln Ile Asp Lys Tyr Cys Tyr Leu Leu Ile Gly Leu Ser
            660                 665                 670

Ser Ala Ala Leu Val Phe Asn Thr Leu Gln His Ser Phe Trp Asp Ile
        675                 680                 685

```
Val Gly Glu Asn Leu Thr Lys Arg Val Arg Glu Lys Met Leu Ser Ala
    690             695             700
Val Leu Lys Asn Glu Met Ala Trp Phe Asp Gln Glu Glu Asn Glu Ser
705             710             715             720
Ala Arg Ile Ala Ala Arg Leu Ala Leu Asp Ala Asn Asn Val Arg Ser
        725             730             735
Ala Ile Gly Asp Arg Ile Ser Val Ile Val Gln Asn Thr Ala Leu Met
        740             745             750
Leu Val Ala Cys Thr Ala Gly Phe Val Leu Gln Trp Arg Leu Ala Leu
        755             760             765
Val Leu Val Ala Val Phe Pro Val Val Ala Thr Val Leu Gln
    770             775             780
Lys Met Phe Met Thr Gly Phe Ser Gly Asp Leu Glu Ala Ala His Ala
785             790             795             800
Lys Gly Thr Gln Leu Ala Gly Glu Ala Ile Ala Asn Val Arg Thr Val
        805             810             815
Ala Ala Phe Asn Ser Glu Ala Lys Ile Val Arg Leu Tyr Thr Ala Asn
        820             825             830
Leu Glu Pro Pro Leu Lys Arg Cys Phe Trp Lys Gly Gln Ile Ala Gly
        835             840             845
Ser Gly Tyr Gly Val Ala Gln Phe Cys Leu Tyr Ala Ser Tyr Ala Leu
850             855             860
Gly Leu Trp Tyr Ala Ser Trp Leu Val Lys His Gly Ile Ser Asp Phe
865             870             875             880
Ser Lys Thr Ile Arg Val Phe Met Val Leu Met Val Ser Ala Asn Gly
            885             890             895
Ala Ala Glu Thr Leu Thr Leu Ala Pro Asp Phe Ile Lys Gly Gly Gln
        900             905             910
Ala Met Arg Ser Val Phe Glu Leu Leu Asp Arg Lys Thr Glu Ile Glu
        915             920             925
Pro Asp Asp Pro Asp Thr Thr Pro Val Pro Asp Arg Leu Arg Gly Glu
        930             935             940
Val Glu Leu Lys His Ile Asp Phe Ser Tyr Pro Ser Arg Pro Asp Ile
945             950             955             960
Gln Ile Phe Arg Asp Leu Ser Leu Arg Ala Arg Ala Gly Lys Thr Leu
            965             970             975
Ala Leu Val Gly Pro Ser Gly Cys Gly Lys Ser Ser Val Ile Ser Leu
            980             985             990
Ile Gln Arg Phe Tyr Glu Pro Ser Ser Gly Arg Val Met Ile Asp Gly
        995             1000            1005
Lys Asp Ile Arg Lys Tyr Asn Leu Lys Ala Ile Arg Lys His Ile Ala
    1010            1015            1020
Ile Val Pro Gln Glu Pro Cys Leu Phe Gly Thr Thr Ile Tyr Glu Asn
1025            1030            1035            1040
Ile Ala Tyr Gly His Glu Cys Ala Thr Glu Ala Glu Ile Ile Gln Ala
            1045            1050            1055
Ala Thr Leu Ala Ser Ala His Lys Phe Ile Ser Ala Leu Pro Glu Gly
        1060            1065            1070
Tyr Lys Thr Tyr Val Gly Glu Arg Gly Val Gln Leu Ser Gly Gly Gln
        1075            1080            1085
Lys Gln Arg Ile Ala Ile Ala Arg Ala Leu Val Arg Lys Ala Glu Ile
    1090            1095            1100
Met Leu Leu Asp Glu Ala Thr Ser Ala Leu Asp Ala Glu Ser Glu Arg
```

-continued

```
                1105                1110                1115                1120
          Ser Val Gln Glu Ala Leu Asp Gln Ala Cys Ser Gly Arg Thr Ser Ile
                          1125                1130                1135
          Val Val Ala His Arg Leu Ser Thr Ile Arg Asn Ala His Val Ile Ala
                     1140                1145                1150
          Val Ile Asp Asp Gly Lys Val Ala Glu Gln Gly Ser His Ser His Leu
                1155                1160                1165
          Leu Lys Asn His Pro Asp Gly Ile Tyr Ala Arg Met Ile Gln Leu Gln
                1170                1175                1180
          Arg Phe Thr His Thr Gln Val Ile Gly Met Thr Ser Gly Ser Ser Ser
          1185                1190                1195                1200
          Arg Val Lys Glu Asp Asp Ala
                          1205

<210> SEQ ID NO 8
<211> LENGTH: 1161
<212> TYPE: PRT
<213> ORGANISM: Arabidopsis thaliana
<300> PUBLICATION INFORMATION:
<308> DATABASE ACCESSION NUMBER: Genbank CAA71277
<309> DATABASE ENTRY DATE: 1997-05-19

<400> SEQUENCE: 8

Lys Gln Ala Ser His Arg Val Ala Lys Tyr Ser Leu Asp Phe Val Tyr
  1               5                  10                  15

Leu Ser Val Ala Ile Leu Phe Ser Ser Trp Leu Glu Val Ala Cys Trp
             20                  25                  30

Met His Thr Gly Glu Arg Gln Ala Ala Lys Met Arg Arg Ala Tyr Leu
         35                  40                  45

Arg Ser Met Leu Ser Gln Asp Ile Ser Leu Phe Asp Thr Glu Ala Ser
      50                  55                  60

Thr Gly Glu Val Ile Ser Ala Ile Thr Ser Asp Ile Leu Val Val Gln
 65                  70                  75                  80

Asp Ala Leu Ser Glu Lys Val Gly Asn Phe Leu His Tyr Ile Ser Arg
                 85                  90                  95

Phe Ile Ala Gly Phe Ala Ile Gly Phe Thr Ser Val Trp Gln Ile Ser
            100                 105                 110

Leu Val Thr Leu Ser Ile Val Pro Leu Ile Ala Leu Ala Gly Gly Ile
        115                 120                 125

Tyr Ala Phe Val Ala Ile Gly Leu Ile Ala Arg Val Arg Lys Ser Tyr
    130                 135                 140

Ile Lys Ala Gly Glu Ile Ala Glu Glu Val Ile Gly Asn Val Arg Thr
145                 150                 155                 160

Val Gln Ala Phe Thr Gly Glu Glu Arg Ala Val Arg Leu Tyr Arg Glu
                165                 170                 175

Ala Leu Glu Asn Thr Tyr Lys Tyr Gly Arg Lys Ala Gly Leu Thr Lys
            180                 185                 190

Gly Leu Gly Leu Gly Ser Met His Cys Val Leu Phe Leu Ser Trp Ala
        195                 200                 205

Leu Leu Val Trp Phe Thr Ser Val Val His Lys Asp Ile Ala Asp
    210                 215                 220

Gly Gly Lys Ser Phe Thr Thr Met Leu Asn Val Val Ile Ala Gly Leu
225                 230                 235                 240

Ser Leu Gly Gln Ala Ala Pro Asp Ile Ser Ala Phe Val Arg Ala Lys
                245                 250                 255
```

```
Ala Ala Ala Tyr Pro Ile Phe Lys Met Ile Glu Arg Asn Thr Val Thr
            260                 265                 270

Lys Thr Ser Ala Lys Ser Gly Arg Lys Leu Gly Lys Val Asp Gly His
        275                 280                 285

Ile Gln Phe Lys Asp Ala Thr Phe Ser Tyr Pro Ser Arg Pro Asp Val
    290                 295                 300

Val Ile Phe Asp Arg Leu Asn Leu Ala Ile Pro Ala Gly Lys Ile Val
305                 310                 315                 320

Ala Leu Val Gly Gly Ser Gly Ser Gly Lys Ser Thr Val Ile Ser Leu
                325                 330                 335

Ile Glu Arg Phe Tyr Glu Pro Ile Ser Gly Ala Val Leu Leu Asp Gly
            340                 345                 350

Asn Asn Ile Ser Glu Leu Asp Ile Lys Trp Leu Arg Gly Gln Ile Gly
            355                 360                 365

Leu Val Asn Gln Glu Pro Ala Leu Phe Ala Thr Thr Ile Arg Glu Asn
    370                 375                 380

Ile Leu Tyr Gly Lys Asp Asp Ala Thr Ala Glu Glu Ile Thr Arg Ala
385                 390                 395                 400

Ala Lys Leu Ser Glu Ala Ile Ser Phe Ile Asn Asn Leu Pro Glu Gly
                405                 410                 415

Phe Glu Thr Gln Val Gly Glu Arg Gly Ile Gln Leu Ser Gly Gly Gln
            420                 425                 430

Lys Gln Arg Ile Ala Ile Ser Arg Ala Ile Val Lys Asn Pro Ser Ile
        435                 440                 445

Leu Leu Leu Asp Glu Ala Thr Ser Ala Leu Asp Ala Glu Ser Glu Lys
    450                 455                 460

Ser Val Gln Glu Ala Leu Asp Arg Val Met Val Gly Arg Thr Thr Val
465                 470                 475                 480

Val Val Ala His Arg Leu Ser Thr Val Arg Asn Ala Asp Ile Ile Ala
                485                 490                 495

Val Val His Glu Gly Lys Ile Val Glu Phe Gly Asn His Glu Asn Leu
            500                 505                 510

Ile Ser Asn Pro Asp Gly Ala Tyr Ser Ser Leu Leu Arg Leu Gln Glu
        515                 520                 525

Thr Ala Ser Leu Gln Arg Asn Pro Ser Leu Asn Arg Thr Leu Ser Arg
    530                 535                 540

Pro His Ser Ile Lys Tyr Ser Arg Glu Leu Ser Arg Thr Arg Ser Ser
545                 550                 555                 560

Phe Cys Ser Glu Arg Glu Ser Val Thr Arg Pro Asp Gly Ala Asp Pro
                565                 570                 575

Ser Lys Lys Val Lys Val Thr Val Gly Arg Leu Tyr Ser Met Ile Arg
            580                 585                 590

Pro Asp Trp Met Tyr Gly Val Cys Gly Thr Ile Cys Ala Phe Ile Ala
        595                 600                 605

Gly Ser Gln Met Pro Leu Phe Ala Leu Gly Val Ser Gln Ala Leu Val
    610                 615                 620

Ser Tyr Tyr Ser Gly Trp Asp Glu Thr Gln Lys Glu Ile Lys Lys Ile
625                 630                 635                 640

Ala Ile Leu Phe Cys Cys Ala Ser Val Ile Thr Leu Ile Val Tyr Thr
                645                 650                 655

Ile Glu His Ile Cys Phe Gly Thr Met Gly Glu Arg Leu Thr Leu Arg
            660                 665                 670

Val Arg Glu Asn Met Phe Arg Ala Ile Leu Lys Asn Glu Ile Gly Trp
```

-continued

```
                675                 680                 685
Phe Asp Glu Val Asp Asn Thr Ser Ser Met Leu Ala Ser Arg Leu Glu
    690                 695                 700
Ser Asp Ala Thr Leu Leu Lys Thr Ile Val Val Asp Arg Ser Thr Ile
705                 710                 715                 720
Leu Leu Gln Asn Leu Gly Leu Val Val Thr Ser Phe Ile Ile Ala Phe
                725                 730                 735
Ile Leu Asn Trp Arg Leu Thr Leu Val Val Leu Ala Thr Tyr Pro Leu
                740                 745                 750
Val Ile Ser Gly His Ile Ser Glu Lys Leu Phe Met Gln Gly Tyr Gly
                755                 760                 765
Gly Asp Leu Asn Lys Ala Tyr Leu Lys Ala Asn Met Leu Ala Gly Glu
    770                 775                 780
Ser Val Ser Asn Ile Arg Thr Val Ala Ala Phe Cys Ala Glu Glu Lys
785                 790                 795                 800
Ile Leu Glu Leu Tyr Ser Arg Glu Leu Leu Pro Ser Lys Ser Ser
                805                 810                 815
Phe Arg Arg Gly Gln Ile Ala Gly Leu Phe Tyr Gly Val Ser Gln Phe
                820                 825                 830
Phe Ile Phe Ser Ser Tyr Gly Leu Ala Leu Trp Tyr Gly Ser Thr Leu
                835                 840                 845
Met Asp Lys Gly Leu Ala Gly Phe Lys Ser Val Met Lys Thr Phe Met
    850                 855                 860
Val Leu Ile Val Thr Ala Leu Ala Met Gly Glu Thr Leu Ala Leu Ala
865                 870                 875                 880
Pro Asp Leu Leu Lys Gly Asn Gln Met Val Ala Ser Val Phe Glu Ile
                885                 890                 895
Leu Asp Arg Lys Thr Gln Ile Val Gly Glu Thr Ser Glu Glu Leu Asn
                900                 905                 910
Asn Val Glu Gly Thr Ile Glu Leu Lys Gly Val His Phe Ser Tyr Pro
            915                 920                 925
Ser Arg Pro Asp Val Val Ile Phe Arg Asp Phe Asp Leu Ile Val Arg
    930                 935                 940
Ala Gly Lys Ser Met Ala Leu Val Gly Gln Ser Gly Ser Gly Lys Ser
945                 950                 955                 960
Ser Val Ile Ser Leu Ile Leu Arg Phe Tyr Asp Pro Thr Ala Gly Lys
                965                 970                 975
Val Met Ile Glu Gly Lys Asp Ile Lys Lys Leu Asp Leu Lys Ala Leu
            980                 985                 990
Arg Lys His Ile Gly Leu Val Gln Gln Glu Pro Ala Leu Phe Ala Thr
        995                 1000                1005
Thr Ile Tyr Glu Asn Ile Leu Tyr Gly Asn Glu Gly Ala Ser Gln Ser
    1010                1015                1020
Glu Val Val Glu Ser Ala Met Leu Ala Asn Ala His Ser Phe Ile Thr
1025                1030                1035                1040
Ser Leu Pro Glu Gly Tyr Ser Thr Lys Val Gly Glu Arg Gly Val Gln
                1045                1050                1055
Met Ser Gly Gly Gln Arg Gln Arg Ile Ala Ile Ala Arg Ala Ile Leu
                1060                1065                1070
Lys Asn Pro Ala Ile Leu Leu Leu Asp Glu Ala Thr Ser Ala Leu Asp
            1075                1080                1085
Val Glu Ser Glu Arg Val Val Gln Gln Ala Leu Asp Arg Leu Met Ala
    1090                1095                1100
```

```
Asn Arg Thr Thr Val Val Ala His Arg Leu Ser Thr Ile Lys Asn
1105                1110                1115                1120

Ala Asp Thr Ile Ser Val Leu His Gly Gly Lys Ile Val Glu Gln Gly
                1125                1130                1135

Ser His Arg Lys Leu Val Leu Asn Lys Ser Gly Pro Tyr Phe Lys Leu
            1140                1145                1150

Ile Ser Leu Gln Gln Gln Gln Gln Pro
        1155                1160

<210> SEQ ID NO 9
<211> LENGTH: 986
<212> TYPE: PRT
<213> ORGANISM: Artificial Sequence
<220> FEATURE:
<223> OTHER INFORMATION: synthetic consensus sequence

<400> SEQUENCE: 9

Met Asp Glu Gly Ala Leu Ser Asp Arg Lys Lys Val Gly Val Leu
 1               5                  10                  15

Phe Arg Tyr Ala Asp Trp Asp Lys Leu Met Leu Gly Thr Leu Ala Ala
                20                  25                  30

Ile Ile His Gly Ser Leu Pro Leu Met Met Ile Val Phe Gly Glu Met
                35                  40                  45

Thr Asp Phe Ala Ser Lys Leu Glu Glu Glu Met Thr Arg Tyr Ala Tyr
 50                  55                  60

Tyr Tyr Ser Gly Leu Gly Ala Gly Val Leu Val Ala Tyr Ile Gln Val
65                  70                  75                  80

Ser Trp Leu Ala Ala Gly Arg Gln Ile Arg Lys Ile Arg Lys Phe Phe
                85                  90                  95

His Ala Ile Leu Arg Gln Glu Ile Gly Trp Phe Asp Ile Thr Gly Glu
                100                 105                 110

Leu Asn Thr Arg Leu Thr Asp Asp Ile Ser Lys Ile Asn Asp Gly Ile
                115                 120                 125

Gly Asp Lys Val Gly Met Phe Phe Gln Val Ala Thr Phe Leu Ala Gly
130                 135                 140

Phe Ile Val Gly Phe Ile Gly Trp Lys Leu Thr Leu Val Ile Leu Ala
145                 150                 155                 160

Ile Ser Pro Ile Ile Gly Leu Ser Ala Ala Val Trp Ala Lys Ile Leu
                165                 170                 175

Ser Phe Ser Lys Glu Leu Ala Tyr Ala Lys Ala Gly Ala Val Ala Glu
                180                 185                 190

Glu Leu Gly Ala Ile Arg Thr Val Ile Ala Phe Gly Gly Gln Lys Glu
                195                 200                 205

Leu Glu Arg Tyr Gln Lys Leu Glu Ala Lys Lys Ile Gly Ile Lys Lys
                210                 215                 220

Ala Ile Ser Ala Ile Ser Met Gly Ala Phe Leu Leu Ile Tyr Ala Ser
225                 230                 235                 240

Tyr Ala Leu Ala Phe Trp Tyr Gly Ser Thr Leu Val Ile Ser Glu Tyr
                245                 250                 255

Thr Ile Gly Ala Met Thr Val Phe Phe Ser Ile Leu Ile Gly Ala Phe
                260                 265                 270

Ser Val Gly Gln Ala Ala Pro Ile Asp Ala Phe Ala Asn Ala Arg Gly
                275                 280                 285

Ala Ala Tyr Ile Phe Lys Ile Ile Asp Asn Pro Ser Ile Asp Ser Phe
290                 295                 300
```

-continued

```
Ser Gly His Lys Pro Asp Ile Lys Gly Asn Leu Glu Phe Lys Asp Val
305                 310                 315                 320

His Phe Ser Tyr Pro Ser Arg Glu Val Lys Ile Leu Lys Gly Leu Asn
            325                 330                 335

Leu Lys Val Ser Gly Gln Thr Val Ala Leu Val Gly Ser Gly Cys Gly
                340                 345                 350

Lys Ser Thr Thr Val Gln Leu Ile Gln Arg Leu Tyr Asp Pro Glu Gly
            355                 360                 365

Val Ile Asp Gly Gln Asp Ile Arg Thr Ile Asn Val Arg Tyr Leu Arg
    370                 375                 380

Glu Ile Ile Gly Val Val Ser Gln Glu Pro Val Leu Phe Ala Thr Thr
385                 390                 395                 400

Ile Ala Glu Asn Ile Tyr Gly Arg Asp Val Thr Met Asp Glu Ile Glu
                405                 410                 415

Lys Ala Val Lys Glu Ala Asn Ala Tyr Glu Phe Ile Met Lys Leu Pro
            420                 425                 430

Phe Asp Thr Leu Val Gly Glu Arg Gly Ala Gln Leu Ser Gly Gly Gln
    435                 440                 445

Lys Gln Arg Ile Ala Ile Ala Arg Ala Leu Val Arg Asn Pro Lys Ile
450                 455                 460

Leu Leu Leu Asp Glu Ala Thr Ser Ala Leu Asp Thr Glu Ser Glu Ala
465                 470                 475                 480

Val Val Gln Ala Leu Asp Lys Ala Arg Gly Arg Thr Thr Ile Val Ile
                485                 490                 495

Ala His Arg Leu Ser Thr Val Arg Asn Ala Asp Val Ile Ala Gly Phe
            500                 505                 510

Glu Asp Gly Val Ile Val Glu Gly Ser His Asp Glu Leu Met Lys Lys
    515                 520                 525

Gly Val Tyr Phe Lys Leu Val Met Gln Thr Gly Ile Asn Ser Glu Ala
530                 535                 540

Met Lys Ser Leu Arg Ser Ser Gln Asp Arg Asp Asp Leu Glu Val Pro
545                 550                 555                 560

Val Ser Phe Trp Arg Val Leu Lys Leu Asn Thr Glu Trp Pro Tyr Val
            565                 570                 575

Val Gly Thr Val Cys Ala Ile Ile Asn Gly Leu Gln Pro Phe Ala Ile
            580                 585                 590

Ile Leu Ser Ile Ile Ala Val Phe Asp Asp Val Lys Leu Leu Leu Leu
        595                 600                 605

Ala Val Val Pro Ile Ile Val Ala Gly Ile Val Glu Met Lys Leu
    610                 615                 620

Leu Gly Asn Ala Arg Asp Lys Lys Leu Glu Ala Gly Lys Ile Ala Thr
625                 630                 635                 640

Glu Ala Ile Glu Asn Ile Arg Thr Val Val Ser Leu Thr Glu Lys Phe
                645                 650                 655

Glu Ser Met Tyr Leu Pro Tyr Arg Asn Ser Val Arg Lys Ala His Ile
            660                 665                 670

Tyr Gly Ile Thr Phe Ser Ile Ser Gln Ala Met Tyr Phe Ser Tyr Ala
    675                 680                 685

Gly Cys Phe Arg Phe Gly Ala Tyr Leu Val His Gly Leu Met Phe Val
    690                 695                 700

Ile Leu Val Phe Ser Ala Ile Val Leu Gly Ala Val Ala Leu Gly Thr
705                 710                 715                 720
```

```
Ser Ser Phe Ala Pro Asp Tyr Ala Lys Ala Lys Leu Ser Ala Leu
            725                 730                 735

Phe Leu Ile Glu Arg Pro Ile Asp Ser Tyr Ser Glu Gly Leu Pro Asp
            740                 745                 750

Leu Glu Gly Val Phe Val Phe Asn Tyr Pro Thr Arg Pro Asp Val Pro
            755                 760                 765

Val Leu Gln Gly Leu Ser Leu Glu Val Lys Lys Gly Gln Thr Leu Ala
            770                 775                 780

Leu Val Gly Ser Ser Gly Cys Gly Lys Ser Thr Val Val Gln Leu Leu
785                 790                 795                 800

Glu Arg Phe Tyr Asp Pro Leu Ala Gly Lys Val Leu Leu Asp Gly Lys
            805                 810                 815

Glu Ile Lys Lys Leu Asn Val Gln Trp Leu Arg Ala His Leu Gly Ile
            820                 825                 830

Val Ser Gln Glu Pro Ile Leu Phe Asp Cys Ser Ile Ala Glu Asn Ile
            835                 840                 845

Ala Tyr Gly Asp Asn Ser Arg Val Ser Asp Glu Ile Val Ala Ala Lys
            850                 855                 860

Ala Asn Ile His Phe Ile Glu Thr Leu Pro Asp Lys Tyr Thr Arg Val
865                 870                 875                 880

Gly Asp Lys Gly Thr Gln Leu Ser Gly Gly Gln Lys Gln Arg Ile Ala
            885                 890                 895

Ala Ile Ala Arg Ala Leu Ile Arg Gln Pro Ile Leu Leu Leu Asp Glu
            900                 905                 910

Ala Thr Ser Ala Leu Asp Thr Glu Ser Glu Lys Val Val Gln Glu Ala
            915                 920                 925

Leu Asp Lys Ala Arg Glu Gly Arg Thr Cys Ile Val Ile Ala His Arg
            930                 935                 940

Leu Ser Thr Ile Gln Asn Ala Asp Leu Ile Val Val Ile Asn Gly Lys
945                 950                 955                 960

Val Lys Glu His Gly Thr His Gln Gln Leu Leu Ala Gln Lys Gly Ile
            965                 970                 975

Tyr Phe Ser Met Val Val Gln Ala Gly Thr
            980                 985

<210> SEQ ID NO 10
<211> LENGTH: 14000
<212> TYPE: DNA
<213> ORGANISM: Arabidopsis thaliana
<220> FEATURE:
<221> NAME/KEY: misc_feature
<222> LOCATION: (3429)...(0)
<223> OTHER INFORMATION: Translation start codon
<300> PUBLICATION INFORMATION:
<308> DATABASE ACCESSION NUMBER: Genbank AP000386
<309> DATABASE ENTRY DATE: 1999-08-03

<400> SEQUENCE: 10
caattaatta tatcaaaatt tcgtatatca tttaaaattc atcactgatt tttgtttaga      60 aaaaagata gatagctatg gacatgacgt cgaattttaa tatatcctat gtaacagtgt     120
tcatataatc aaaaagaaa aataattac tattgtttgt gttctttgca acaatgcgtt      180
agaaactcgg agaccacttg ttttttctct tatgatttcg cttcagtatg atttagcaaa    240
gcatctctac ggtacaaaat atcttacgaa ttgacatgat ctgatccaca ctatatcaag    300
gagttagaaa gacagaactg aaagcttctt agctcgatat gtatttcaag ctacggttca    360
caccatctag ggagacaaga atggaagaag gcatgacgtc aagtcgaact atgcagctct    420
```

-continued

```
cttacttaaa tgggtcgaca aacaaatacg gaaccaacta tcatccattc gagcaagcgg    480
tgataggtgg tatgactaag gtctctaaat ttggtttacg gcgaaaaatt aattgatcaa    540
aaaattttg gtttagtgtt ttaagatctt tttcaaaaaa acgttgtatt tgatgtataa     600
acgctatttc tttttgaaat taatttaata ttattttgt ttgaaaagaa gaagaaacat     660
aattcaaaca atccctatct ttaatgttcc aacatcttaa taaatacata attaaaactc    720
tacgatcaat actacacttc tgacgattat taaatcgcat cgtcgtacac tattattaca    780
aagaccgttc tatctacatt aatattcttt atatatttt ttttttcatt ttttgagatt     840
gttggagtat atatccttag attttcttgt atataaaaat agataattat aatgggataa    900
acgaaacatc gttgaagccg tgaagtggca ttggtctaca ccagagcaac acaaaaagac    960
aaccacttca catggtctgc tcttacattc ataaccgaat ctaagtcact tttagttggt   1020
tgtaattttg taactattat tccaacacct ctttttttac tttttagatt gttttataat   1080
agaaatattt taattcctaa attaataatg aaagtaaatg taatatgagt cagtacaata   1140
tgtgaaaaac ttaaaaagtt gacagaattt agcatttgat taaagtgta tgaagaagaa    1200
gaaaaaagaa gatcttttg tatctataga tttagtgcat aacttttctc agattttcga    1260
tatatacaag aatttaacat aagaaaaatc aagacaaatg gacctggtta taatcggtta   1320
tctgttgtaa atattatatt tcatattctt ctccacttca taattcttat tggagttcct   1380
tcaccaaatg tttgatgttc cattaaatta atctaccact ctaataagag gtatcgtact   1440
acaaattaca cttcataaac aagagaagaa cataaatttg aatttttta aaaaaacata    1500
tgcgttataa caccaaacag taacggacta gctgatcctt gaatttatat tagttgcaaa   1560
aatttatata tcgaaattga aacatgaatt tttaaaatta ttagaaaatg tatgatgttg   1620
tctaaatgtg acattacaaa tacatgatgt tgtttaaaaa ttattataaa acaaccaaag   1680
tttggcgtca ttctggtaaa cgcacttaat gaatttatat acagttaaag attttaacat   1740
caaatttaa aatgacaact taactaaaat ttgtatccta atattttac tagagaaact     1800
cacacatatt tttcaaacaa atgattagtt atatatcctt cgataatagg tattgtgtaa   1860
aactgtgtgg tttgcacaag tgatccctcg atattctttc tgctaaagat cgacttccca   1920
cagtttcgat atctcgggtt tgggtgcaat agcatatgct tgtttagtat gcagataatc   1980
gtatgagaga gtcagagaga tcatctattt tcatgatat ggtctgagct aatcgatcat    2040
ttgttatta tactcgataa cgttctaatt tgtatgattt ttcagccttg atctatcaca    2100
aaatggagat aatgaaatgg tagtcataag aaaggtaatg atcccttga catgcttatt    2160
ataacacaaa aagtaatcgc tactgattag cttaccctat gatttgaatc atataacttt   2220
atactaattg tctaagtgtg atgatataat gtatatgatg tcatttataa cttattagta   2280
aaaatataaa gttcttcatc attgtcataa ggagttaatt ggatatacat caaaaaattt   2340
cctaaattt tagaaattat taatcaagtt ataatagaaa ttattaaata aaatatatga    2400
tgtttctaa atgtgacgat acaaaataca tgatgttgtt caaaacttat tagacagaaa    2460
ccaaagtaca tcatcattgt gatgaagact ttaatggatt tatacatttc aaagtttaa    2520
acattactta tttaaatgaa aaattgagct aaaatttgta tacttatatg ttgaccatag   2580
aaatacttct atataatttt agacaagttg tctatacata tatatatata tatatatata   2640
tatatatatg tatttacaca aaaatcaagt tttcttaatg taacaatata aaatatataa   2700
atatctaatg ttgtttaaaa attatttaga ccaaaaaaaa aaaaaactgt aatcaaactt   2760
```

-continued

```
tcattggatt atatctaact ctaaacatga attttatac aatgacatgt tcaataaaat    2820
tcccatttca tagtttgacc agaaaaaatg cttgcagatt tgttaaaatc tctacttatg    2880
caaaaccatt gaatcacacc agattttgat ttgtagtact ttaaaaatat taattgaaca    2940
caacataact ttaacaaaaa agatctttat aaaaaaaaaa ctttctaaaa tgacattaat    3000
taacacaaat tagtcaattc aaacaatcca ataaaatcaa agtaaaccct taattgtttt    3060 tttttttccat tttacaaaat gttaaacatt aattacatca actagcaaca cgaatctctc    3120
aatctctcat gtctcaatga gtctttgacc actagtcttc atcactctct ctccctccta    3180
tatataccaa tcacaccctt ctccaaccac actctcattc tctctctctt ctcaccactt    3240
caaaacaaga cactcgtaaa agagttcttg aacttcacaa acaattgtc agattttcaa    3300 gaaaactttt ataaaacaaa aaacatttca ttctttctct ctctctctct cactgctcaa    3360
tgatctcgtt ttctcactaa accaactcgt ttcttcttac ttttctttaac tcggatctac    3420 aaaaaaccat gtcggaaact aacacaaccg atgccaagac tgttccagca gaagcagaga    3480
agaagaaaga acagagttta ccattcttta aactcttttc tttcgctgat aaatttgatt    3540
atctcttaat gttcgttggt tctcttggtg ccattgttca tggctcttcc atgcctgtct    3600
tctttttact ctttggtcaa atggttaatg gatttggtaa aaaccaaatg gatttacatc    3660
aaatggttca tgaagtctct agagtaagtc ttttttttct ttcttgtttt tatcaaatta    3720
gatccaagat ctgatctaat ttttgtgttt gtgaaatttt gcagtattct ctatatttcg    3780
tctacttggg tttggtcgtt tgcttctctt cttacgcagg tttgtttctt acaaatccaa    3840 tcttctttt ctttattctt caatcaagaa acccagtaat taaatcacat tataaacaag    3900
atcaagaaat tttttgcaca aaaaaaaaag aaaacaagat caagaaatta taaagttta    3960 gattaaacat ttgcattatt ttctttttttt tggttcaacc aattaaccca ttaacataaa    4020
ttaaatcaga ttattaggca agaaatctaa aggtgtattt tttgagtttt atttgattct    4080
tcctcaaagt gaccatttac tctgaaggta aaacatttt ttttactcta caacaaaaac    4140
ccaacttctt tttttgtttg cttcaaaatt atattaaaaa aagaaagctt aaactttgtt    4200
taaaatcttg ttttttttgt cattcgcttt tgattagaac taaaaaacc atttttatag    4260 aatgttgttt acataagtga tgtaatgggg ttcggaacga actttccgtg ccaaccgctt    4320
ttatagacaa gaaatctaaa ggtgtaattt ttgagttttt atttgattct tccacaaagt    4380
gatcatttac tctggtaaac attttttttac tctacaacaa aaaccaaact tttttatgtt    4440
tgcttcaata aataaaaacc tagaaacaga aatcacaatc tagagagaat caaaattata    4500
tataaaaaaa aaacacttca aattttaaa aattttaata tgttaaaagg ataagccaag    4560
tccacgtgat tcatggacta ctactttgtc tatatcgaaa aaaaaaaaaa aatgggcatc    4620
tctctcacat ttattacaac ttcataaaaa ttcttgtaat aataaccata attttttgtt    4680
aaataatttt acagagatag catgttggat gtattctgga gaaagacaag tagcagcatt    4740
aaggaagaaa tatcttgaag cagtattaaa acaagacgtt gggttctttg atactgatgc    4800
tagaactggt gacattgtct ttagtgtttc tactgatact cttcttgttc aagatgccat    4860
tagtgaaaag gtaaccattt tttttttttac taccaacaaa atctagtatt taccggcggg    4920
tcccattttt ttcatgatca atctttatca aagttttggg tccgtttatg ttagcaaccg    4980
tcgtttatct tgcgcctcag gtggttaggg aagaaaaaag actatagatt gattttttt    5040 tttgttaaaa taaagttgg attttttca taagattgtg aaaataagta atttttttt    5100 acaaatttgc tatagaaata gaggatttt ttcactattt aactaaaact taaatgatat    5160
```

-continued

```
agtactcatt ttcttacatt tttaatataa aaatagcttc ttttttttcca ttgtgaaaaa    5220
tatttattat gcaaaataat gtttctttaa caagtaaaat aaatatttgt tattaaaaaa    5280
aatgtgtaaa gtaccttcaa attttaatag tacatttat ctaaaactgt tttttttttt    5340
gcaatttggt cctgtctctg tggtgcacgt tagcaagcac gagctaacat gcactgggtc    5400
ccctagtttc attattatca tcactctttt ttattgttga tgaagtgaat taataacaga    5460
gtagttgaaa aaaaattgaa tttctcaggt tggaaacttt atacattacc tctcaacatt    5520
tttggcggga ttagtagttg gatttgtatc agcatggaaa ttagctttgt taagtgttgc    5580
tgtgattccc ggaatcgctt tcgccggagg tttatacgct tatacactca ccggaattac    5640
ttcaaagagc cgtgaatctt atgctaacgc cggtgttatc gccgagcagg taaataaaga    5700
ttaaagtttg ttcctttatt tgttttattt aatgcccacc aactgttcga cgtaatgctt    5760
tttaactgtt cttaggcttg cttctttgta cttgatctct caaatgattt ttttttttttt    5820
tcattgcttc ttatgcaatc caaagactta aacagtgttt tcactaattc aaaatctttg    5880
cttttctttg gtcggttaat gattgatgtt ttggtttctc aggcaattgc tcaagttcga    5940
actgtttatt cttatgttgg agagagtaag gcacttaatg cgtattcgga tgcgattcag    6000
tatacgctta agctcggtta taaagcgggg atggctaaag ggttgggttt aggatgtact    6060
tatggaatag cttgtatgtc atgggctttg gtgttttggt atgctggagt ttttattcgg    6120
aatggacaaa ccgatggagg aaaggcgttt actgctatat tctctgctat tgttggtgga    6180
atgtaagaat tcaaaacata acaatgatgt ggttttgtgt attttgtgtt ttgttattac    6240
ttggatgtca cttttttgttt ctgtgtgtgt ttttaggagt ttgggggcaat cttttctcgaa    6300
tcttggggcg tttagtaaag gtaaagcggc tggttataag ttgatggaga taattaacca    6360
gagaccgacg ataattcaag acccgttgga tggaaaatgt ttggatcaag ttcatgggaa    6420
cattgagttt aaagatgtga cttttagcta tccttcacgg cctgatgtta tgatcttcag    6480
gaactttaat attttcttcc cttctgggaa aactgtggcg gttgttggtg ggagtggctc    6540
tggaaagagt actgttgttt ccctcattga gagattctat gatccaaaca gcggtaattt    6600
gattgaattt gttttttgct atttgagtct ttggctagtg actggatcat aactttgttt    6660
atttttttctt gatgagcagg gcaaattctg ttggatggtg ttgagataaa gacgcttcag    6720
ttgaagtttt tgcgtgaaca atcgggcctt gtgaatcaag aacctgcgct ctttgccact    6780
actatactag agaacatact ctatggaaag cctgatgcaa caatggttga agttgaagct    6840
gctgcttccg ctgcgaatgc gcatagtttc attacattac ttcctaaagg ctacgacaca    6900
caggtataaa tcaaatattt gattatatgt ctagttaatg tcatggcctt ttgcttaatt    6960
ttttgttgaa tgtcaataca attaggttgg agaacgtggt gttcaactct caggtggaca    7020
gaagcagaga attgcaattg ctagggcgat gttgaaagac ccaaagattc tgttactaga    7080
tgaagctaca agcgctcttg atgctagctc tgagagcatt gttcaggaag ctttagacag    7140
agtcatggtg gggaggacca ctgttgttgt tgctcatcgt ctctgcacca tcagaaatgt    7200
tgattccatt gccgtgatac agcaaggcca agttgttgaa accggaacac atgaagaact    7260
cattgccaaa tccggtgctt acgcatccct catcaggtttt caggaaatgg ttggtactcg    7320
agatttctca aacccgtcaa ctcgtcgcac tcgttcaacc cgtttgagcc attcactgtc    7380
aacgaaatca ctcagtttaa gatcaggaag tttgaggaat ctgagctatt cttacagcac    7440
tggagctgat ggtcggatag agatgatttc aaatgcagag actgaccgaa agactcgtgc    7500
```

```
ccctgaaaat tacttctaca ggcttctcaa gcttaattca ccggaatggc cttactcaat    7560
catgggagca gtaggctcaa ttctttctgg tttcattggt cctacatttg ctattgtgat    7620
gagcaacatg atcgaagtct tctactacac agactatgat tcaatggaaa ggaaaacaaa    7680
agagtatgtc ttcatctaca ttggtgctgg tctctatgct gtgggtgctt atttgatcca    7740
acattacttc tttagcatca tgggagaaaa cctcacaaca agagtaagaa gaatgatgct    7800
ctcaggtatg tatcaaaatc tcctgaattt gcttaaaatc actttcccat ttcttatttt    7860
ggtttcttga ttgttcttat ttagctatct tgagaaacga agttggttgg ttcgatgagg    7920
atgaacacaa ctcaagcctg atcgctgcac gtttagctac tgatgcagca gatgttaaat    7980
ccgctatagc cgagagaatc tcagtaattc tacaaaacat gacttcactt ctcacatcct    8040
tcatagtcgc cttcatagta gaatggagag tctcacttct catcttaggc acattcccac    8100
ttctagtcct cgctaacttt gctcaggtaa ataatctaat cttttactc aaaatctttc     8160 aatattcatc aatcattaaa atataattgg aatcttgcat tcaccattat gatcttaaga    8220
aaaaacgaca aaggccaga ttttataaa tttatatttg cttttcaaaa gttcaaaact      8280
ttatagaaca tggcaacaca gccactgcct ctacacgtgc ttcatcttct aactttatcc    8340
aagtttgcat ttatgtttac aataataatc ataaagaat tattaagaag ctttttttt      8400 ctacttttg gaaatagtgt aagggtcaag atcatggagc cctcacatca ataaatgtgc     8460 taaaaaatt aaaaaacagt aggctttagt ttactctctg ggcatgtgtg aagaatattt     8520
attatatagt ttctattggt actatgaccc atagataaca gtgttcacga aaatagctaa    8580
gattcctctg tcttttgctt ctgctaaatc tatcctactt taagctttca tatttacttc    8640
actctctgaa ctctgaactg tgatcccact tctctcttta tttaattctt ttgcccataa    8700
aacctcacca caaaaatcca aaaaatctgc aattttttc cttcttagaa ccaatatttt     8760
atttagagtt cttcattggt caaagttgtt gtctcagtgc attatttact tatcacagtg    8820
tgtgtgtcag tgtttttaca ccatccacta gtcaatgttt gcttgtgggt ttctttgttt    8880
tggtagatta ggttgtgatg agtttttttt ttgtttctaa ctagctgcaa ggttcaggac    8940
tctgctttga tatatcacca acatttttc acccgtgatc taattattag ttgaaaaatc     9000
tatcaaatag atttcacaca gaagaacata gataggcatt gtacttgtac tgatgttgat    9060
gggatagagt gttgcatatg tgatttaact atatggttct acgtcatgtt ttagtggcga    9120
cttagacctt tgattgtcaa tcttattttt tacaagtgaa ctattattac catctgttgt    9180
tctaaatcat aagtattaat atatgtggct acattgcagc aactatctct gaagggtttt    9240
gctggagaca cagctaaggc tcatgcaaag acttcaatga ttgctggtga aggagtcagt    9300
aacattagaa ccgtagcagc tttcaatgca cagagcaaga ttctctcttt gttctgtcat    9360
gagcttcgtg tacctcagaa agaagcttta taccgaagtc aaacctcggg tttcctattt    9420
ggcctctcgc agcttgctct ctatggttct gaggctttaa ttctctggta tggtgcccac    9480
cttgtgagta aaggcgtgtc aaccttttcc aaagtgatca agtgtttgt ggttttggtc     9540 attactgcaa actctgttgc tgaaactgtc agtcttgctc ctgaaattat tcggggaggt    9600
gaagctgttg gttcggtttt ctcggtcttg acaggcaga ccaggattga cccggatgat     9660
gctgatgctg atcccgtgga gacgatccgt ggagacattg agtttaggca tgttgatttc    9720
gcttaccctt caagacccga cgtcatggtt ttcagggact ttaacctcag aattcgagct    9780
ggacatagcc aagctcttgt gggcgcgagt gggtcaggga gagttctgt aattgcgatg     9840 atcgagcggt tttacgaccc tcttgctgga aaagtcatga ttgatggcaa agacatccgc    9900
```

```
cggctaaacc tgaaatctct aaggctcaaa atcggtcttg ttcaacaaga accagctctc    9960
ttcgcagcaa cgatcttcga caacatcgcc tatggtaaag atggtgcaac tgaatccgag   10020
gtaattgatg cagctcgagc cgcaaatgct cacggtttca tcagtggttt acctgaaggt   10080
tacaaaactc cagtaggcga aagaggagtg cagttatcag gtggacagaa acagaggatc   10140
gcgatagcaa gagctgtgct caagaaccct acagtgttgc ttctagacga agcaactagc   10200
gcactagatg cagaatcaga atgcgtgctg caagaggcgt tagagaggct catgagaggt   10260
cggaccaccg tggtagttgc tcaccgcttg tccaccataa gaggtgttga ttgcattggt   10320
gtgattcaag acgggcggat tgtggagcaa ggcagccatt cagagctcgt tagccgacca   10380
gagggagctt attcaaggct gttacagctt caaacacata ggatttgaag cttgatcatg   10440
gattaaaaac aaaaaatcgg tttgtgtaat ttttttttata ttaaaacttt aatttggaag   10500
atttctatgg actataacga taatatgaat aggtgtagat aatgaagctt ttggagtgtt   10560
tatgaaggtt ctttaattaa gggttatttt tttcgcattt tgcttatgtg cccgttttgg   10620
aacataagac tgaactatgt tttcgttatg tttttaattt atgcctcgaa acaaaacaaa   10680
atcactctaa tactttggtt gatcaaaatt tccctaaaac atttggttca tgactagaat   10740
tgatcggaca tgttctttta ggggtttgat ctcgcatggt ctaatcaggt tatgtggtct   10800
tacagcgact taatcaattt agaccggcta tcaaaattag attcagccta aacagcaaaa   10860
ttgtcttata taatatccta aatcacagac cggattttttt tttttttataa actctatcgg   10920 ctgatccggt caacccggt agaaacgcac tgaagtgttt catagtggac ttcaaaccga   10980
aattttgcag aaattgagat gagaatgagc tctacctcgc attgacatgt tatttcgttc   11040
ttgagatctt aagtaatttt ttgagatctt aagtaatttt ttggtattca agttccttat   11100
ttttttgcgg ttactcgtct tgacatgtta tttcgttctt gtgctactta cataccacaa   11160
tatatgtagg tttctaaaca tatataatag gaatgttgtt ctatatatgt gttgtttgat   11220
acgtaaagag taatctggtt ctacgtagag tctatctctt gtttcttggt gagattttga   11280
ctggactgca tggtaatcct cgcgcatggt gtttagttac cggttgcttc attcatttgg   11340
ccacgctcaa atttttctaga agactcttcg gtctttggta caaaggcctc cgattttttcc   11400 atgacaagtt cattcatatt tttttgtgac aacttgattg ttgttcattt ccgaatattc   11460
catgaacgta tcaaactcaa taaaatcgat tgttgtcact cccctttaaga tgagatcctc   11520 aacggcagct tcaccactag ccatgttttc acacatgatc aactatctca cattttttact   11580 aaggctttaa gcaggaatat tacttctaga attttaacaa tctagaattt ctagaggaaa   11640
tgttcacatg tatataatttt ggtatatgat ctagagaact tatataagat tatcaatgtt   11700
taatatactc aacaaatggg ttcttctatt ttatcttcta attgttgggg ccttgaatta   11760
tttagttctt tttcactatt cctttttcttt tatttggtgt gtggagccat aaagttccaa   11820
taatttctat gaaagaaat gaataaaatc taaagaaacc aactgtgaag ctctttaatc   11880
ttattctatc tgttggatct gttttgccttt atttgctttg catgtggttt tgctgtttaa   11940
gataaaggcc atatcttctc ctaattcttt ttccaaatca acacatcaaa tatataaaag   12000
actccaaata ttttgaatag aatcataatt tatttaatta caaaaaaact taagaattc   12060 aagacctgcg atcacaagac aaatacatgt aaggaattaa atatttaaga taccaaccgc   12120
taataaataa gactcacaat ttctaaaaat taaaacgaaa aaaagaaaaa attagtcatc   12180
attgcatatc ttagtgaaca aaaatcaata agaaaaggat aatatacttt ttaccaacat   12240
```

```
cacataaacc taaaagcatc tcacaccaaa agtaaattaa aaactcagaa aaagctgaat    12300
acaagttatg aattttatgg aaagtgttag tgtgttagtg ttgttatcat tacaacttta    12360
aaataattat gaacatgaaa aaatagattg aacatgaagc agcattggga aggactcgaa    12420
tgtccctact catactgaca aaacctcaag tgttccagtg cgttaggttt cactttccag    12480
tagtatgtgt atctgctttt tttgtatata ttaatgtaat agatagtgta gagaatcatg    12540
aggaacattt tgtaatcata gaactaaggc ataattttga tcgtgtgaaa taatactatt    12600
atttttggta acaaggatga tctggaccga attccgacta attttccagg tgaatatagt    12660
catcaagtaa cttgatcacc ggattttaaa aatgaattat gaacatgata tcatttcaac    12720
taatcaaata aaaatgaaaa aattcatgtg ggaatcatat ccctcaaatc tgttaccacc    12780
aaactacttt catttggttt gtgtgagaaa tataagaatt atcaaacaaa gaaaaggtt    12840 ttgcttaatt ataatgatat gaggttcatc aaatttatat accactaaaa tattcctaca    12900
ctcatccaaa tattattctc gcttatgcag ttttaatcta atgtacaaat catatccata    12960
agcgcattgg ccgatgctaa aattttggca ttagttgttg atttgttttt cttgagtcct    13020
atgttcaaaa aatatatttg ataatttaat gtataaatta tacccataat cacattgatc    13080
aatgcttaaa gttttgtatt agttgttgat ttttgtttg tttgcgtgtg ttgaattttc    13140
ataaatgaaa agtaaatacg ataatcatat ttcaaaacgt aaggtgtta attagtagtc    13200 taaatggtaa aatataaaca gtatattata aaaattacta aaatggtttt gtaaaaaaa    13260 tatgctattt gtattataat gaaattcaaa aattttaaat agaacgtata atttctgcac    13320
aaagaggttt tgaggtgtta taattcatga agtaaatttt atttactgac gggtaagttg    13380
tgaaaaagtt tgaagactat ttttttttgct tttcacagag aaaactactt tccttttta    13440 ttgtatgatg agaaggcaaa agtgcagaca tgtgctttct tttctcccat tttcaacaat    13500
gtcactcgtt gtattattca tattttagca aactggttat atctatatct atcaatcatt    13560
tcagaacatc atatccatca gttttttggac attgctacat acgttagtat tgatgtacca    13620
gttaccctaa caggcttttg catagtgtgg cagaacacgt gaggtgtgat atatgcggat    13680
gaattctatg ttctgcattt tgttaccatt catataaaag tattgtttta gttgtgctgc    13740
ggtttaagtc ctaatacaga tttatttgta gtgttatgtt tataaaccac attggaaccc    13800
aaactctaag agaatataag atcaatgtgt aattaataaa ttttatagtc attcggataa    13860
aacttagaaa gataacaaaa gtaagaacga gtatttttaa gcgaatactc tttagatatt    13920 cttttgtattg atcattattg acaaaccatt aaacattttt gtagaccta aaatccgata    13980 tccaaaaaac aattcttatt                                                 14000
```

<210> SEQ ID NO 11
<211> LENGTH: 29
<212> TYPE: DNA
<213> ORGANISM: Arabidopsis thaliana

<400> SEQUENCE: 11
cactgctcaa tgatctcgtt ttctcacta                                        29

<210> SEQ ID NO 12
<211> LENGTH: 30
<212> TYPE: DNA
<213> ORGANISM: Arabidopsis thaliana

<400> SEQUENCE: 12
cttgaatcac accaatgcaa tcaacacctc                                       30

```
<210> SEQ ID NO 13
<211> LENGTH: 29
<212> TYPE: DNA
<213> ORGANISM: Artificial Sequence
<220> FEATURE:
<223> OTHER INFORMATION: PCR primer

<400> SEQUENCE: 13
cattttataa taacgctgcg gacatctac                                            29

<210> SEQ ID NO 14
<211> LENGTH: 29
<212> TYPE: DNA
<213> ORGANISM: Artificial Sequence
<220> FEATURE:
<223> OTHER INFORMATION: PCR primer

<400> SEQUENCE: 14
tttctccata ttgaccatca tactcattg                                            29
```